(12) United States Patent  (10) Patent No.: US 8,562,802 B1
Beaudet et al.  (45) Date of Patent: Oct. 22, 2013

(54) TRANSILLUMINATOR BASE AND SCANNER FOR IMAGING FLUORESCENT GELS, CHARGING DEVICES AND PORTABLE ELECTROPHORESIS SYSTEMS

(75) Inventors: Matthew Beaudet, Eugene, OR (US); Ilana Margalit, Ramat Gan (IL); Ronen Benarieh, Kibotz "Givat brener" (IL); Andres Wainstein, Tel Aviv (IL); Gustavo Turkieltaub, Tel Aviv (IL)

(73) Assignee: Life Technologies Corporation, Carlsbad, CA (US)

( * ) Notice: Subject to any disclaimer, the term of this patent is extended or adjusted under 35 U.S.C. 154(b) by 136 days.

(21) Appl. No.: 13/213,953

(22) Filed: Aug. 19, 2011

Related U.S. Application Data

(63) Continuation-in-part of application No. 11/764,170, filed on Jun. 15, 2007, which is a continuation-in-part of application No. 11/674,657, filed on Feb. 13, 2007, now abandoned.

(60) Provisional application No. 60/829,513, filed on Oct. 13, 2006, provisional application No. 60/773,026, filed on Feb. 13, 2006.

(51) Int. Cl.
*G01N 27/447* (2006.01)
*G01N 27/453* (2006.01)

(52) U.S. Cl.
USPC ............................ 204/466; 204/456; 204/606

(58) Field of Classification Search
USPC .................................. 204/450–470, 606–621
See application file for complete search history.

(56) References Cited

U.S. PATENT DOCUMENTS

| 4,520,110 A | 5/1985 | Stryer et al. |
| 4,542,104 A | 9/1985 | Stryer et al. |
| 4,603,209 A | 7/1986 | Tsien et al. |
| 4,657,655 A | 4/1987 | Smoot et al. |
| 4,714,763 A | 12/1987 | Theoropulos |

(Continued)

FOREIGN PATENT DOCUMENTS

| EP | 1065250 | 12/2004 |
| WO | WO97/40104 | 10/1997 |

(Continued)

OTHER PUBLICATIONS

Gaugain, "DNA Bifunctional Intercalators 2. Fluorescence Properties and DNA Binding Interaction of an Ethidium Homodimer and an Acridine Ethidium Heterodimer", *Biochemistry*, vol. 17 No. 24, 1978, 5078-5088.

(Continued)

*Primary Examiner* — J. Christopher Ball

(57) ABSTRACT

Cassette electrophoresis systems that allow viewing of molecules during the electrophoresis run are disclosed. Cassette electrophoresis bases that reversibly engage light sources, such as light source bases are disclosed. Also disclosed are visible light transillumination systems for viewing a pattern of fluorescence emitted by fluorophores comprising a cassette housing fluorophore-containing material and a base unit to support the cassette. In some aspects the base unit that includes a power supply also houses a light source having output in the visible wavelength region and a filter placed between the light source and the fluorophores. The system is constructed and arranged such that patterns of fluorescence emitted by the fluorophores are viewable. Also described are charging devices for providing charge to gel electrophoresis systems, portable gel electrophoresis systems and methods of use thereof.

18 Claims, 23 Drawing Sheets

(56) References Cited

U.S. PATENT DOCUMENTS

| | | |
|---|---|---|
| 4,774,339 A | 9/1988 | Haugland et al. |
| 4,786,813 A | 11/1988 | Svanberg |
| 4,810,636 A | 3/1989 | Corey et al. |
| 4,812,409 A | 3/1989 | Babb et al. |
| 4,849,362 A | 7/1989 | Demarinis et al. |
| 4,859,582 A | 8/1989 | Stryer et al. |
| 4,883,867 A | 11/1989 | Lee et al. |
| 4,945,171 A | 7/1990 | Haugland et al. |
| 4,957,870 A | 9/1990 | Lee et al. |
| 4,981,977 A | 1/1991 | Southwick et al. |
| 5,055,556 A | 10/1991 | Stryer et al. |
| 5,132,432 A | 7/1992 | Haugland et al. |
| 5,187,288 A | 2/1993 | Kang et al. |
| 5,227,487 A | 7/1993 | Haugland et al. |
| 5,242,805 A | 9/1993 | Naleway et al. |
| 5,248,782 A | 9/1993 | Haugland et al. |
| 5,268,486 A | 12/1993 | Waggoner et al. |
| 5,274,113 A | 12/1993 | Kang et al. |
| 5,314,805 A | 5/1994 | Haugland et al. |
| 5,410,030 A | 4/1995 | Yue et al. |
| 5,433,896 A | 7/1995 | Kang et al. |
| 5,436,134 A | 7/1995 | Haugland et al. |
| 5,442,045 A | 8/1995 | Haugland et al. |
| 5,449,446 A | 9/1995 | Verma et al. |
| 5,451,343 A | 9/1995 | Neckers et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,507,287 A | 4/1996 | Palcic |
| 5,534,416 A | 7/1996 | Millard et al. |
| 5,569,587 A | 10/1996 | Waggoner |
| 5,569,766 A | 10/1996 | Waggoner et al. |
| 5,582,702 A | 12/1996 | Cabilly et al. |
| 5,582,977 A | 12/1996 | Yue et al. |
| 5,606,502 A | 2/1997 | Adachi |
| 5,616,502 A | 4/1997 | Haugland et al. |
| 5,627,027 A | 5/1997 | Waggoner |
| 5,647,368 A | 7/1997 | Zeng |
| 5,658,751 A | 8/1997 | Yue et al. |
| 5,696,157 A | 12/1997 | Wang et al. |
| 5,798,276 A | 8/1998 | Haugland et al. |
| 5,808,044 A | 9/1998 | Brush et al. |
| 5,830,912 A | 11/1998 | Gee et al. |
| 5,846,737 A | 12/1998 | Kang |
| 5,863,753 A | 1/1999 | Haugland et al. |
| 5,865,974 A | 2/1999 | Cabilly et al. |
| 5,877,310 A | 3/1999 | Reddington et al. |
| 6,002,003 A | 12/1999 | Shen et al. |
| 6,004,536 A | 12/1999 | Leung et al. |
| 6,008,373 A | 12/1999 | Waggoner et al. |
| 6,008,379 A | 12/1999 | Benson et al. |
| 6,043,025 A | 3/2000 | Minden et al. |
| 6,127,134 A | 10/2000 | Minden et al. |
| 6,130,094 A | 10/2000 | Waggoner et al. |
| 6,130,101 A | 10/2000 | Mao et al. |
| 6,133,445 A | 10/2000 | Waggoner et al. |
| 6,162,931 A | 12/2000 | Gee et al. |
| 6,339,392 B1 | 1/2002 | Ashihara et al. |
| 6,379,516 B1 | 4/2002 | Cabilly et al. |
| 6,428,667 B1 | 8/2002 | Glazer et al. |
| 6,562,632 B1 | 5/2003 | Szalecki et al. |
| 6,664,047 B1 | 12/2003 | Haugland et al. |
| 6,716,979 B2 | 4/2004 | Diwu et al. |
| 6,967,251 B2 | 11/2005 | Haugland et al. |
| 6,974,873 B2 | 12/2005 | Leung et al. |
| 6,977,305 B2 | 12/2005 | Leung et al. |
| 2002/0089658 A1 | 7/2002 | Seville et al. |
| 2002/0112960 A1 | 8/2002 | Cabilly et al. |
| 2002/0134680 A1 | 9/2002 | Cabilly |
| 2003/0104386 A1* | 6/2003 | Kuhr et al. .................. 435/6 |
| 2004/0171034 A1 | 9/2004 | Agnew et al. |
| 2005/0074796 A1 | 4/2005 | Yue et al. |
| 2005/0082168 A1 | 4/2005 | Kang et al. |
| 2005/0121325 A1* | 6/2005 | Updyke et al. ............ 204/469 |
| 2005/0208534 A1 | 9/2005 | Dallwig et al. |
| 2005/0214810 A1 | 9/2005 | Dallwig et al. |
| 2005/0244976 A1 | 11/2005 | Gee et al. |
| 2006/0141554 A1 | 6/2006 | Gee et al. |

FOREIGN PATENT DOCUMENTS

| | | |
|---|---|---|
| WO | WO99/51702 | 10/1999 |
| WO | WO01/21624 | 3/2001 |
| WO | WO02/26891 | 4/2002 |
| WO | WO2005/121325 | 12/2005 |

OTHER PUBLICATIONS

Gaugain et al., "DNA bifunctional intercalators. 1. Synthesis and conformational properties of an ethidium homodimer and of an acridine ethidium heterodimer", *Biochemistry*, vol. 17, No. 24, 1978, 5071-5078.

Haugland, "The Handbook; A Guide to Fluorescent Probes and Labeling Technologies", *Tenth Edition, CD-ROM*, Invitrogen / Molecular Probes Invitrogen Detection Technologies, 2005, 1-1126.

Markovits et al., "Dynamic Structure of DNA Complexes. Fluorometric Measurement of Hydrogen-Deuterium Exchange Kinetics of DNA-bound Ethidium Dimer and Acridine-Ethidium Dimer", *Biochemistry*, vol. 22, No. 13, 1983, 3231-3237.

Markovits et al., "Effect of B-Z transition and nucleic add structure on the conformational dynamics of bound ethidium dimer measured by hydrogen deuterium exchange kinetics", *Nucleic Acids Research*, vol. 13, No. 10, 1985, 3773-3788.

Rye et al., "High-sensitivity two-color detection of double-stranded DNA with a confocal fluorescence gel scanner using ethidium homodimer and thiazole orange", *Nucleic Acids Research*, vol. 19 No. 2, 1990, 327-333.

* cited by examiner

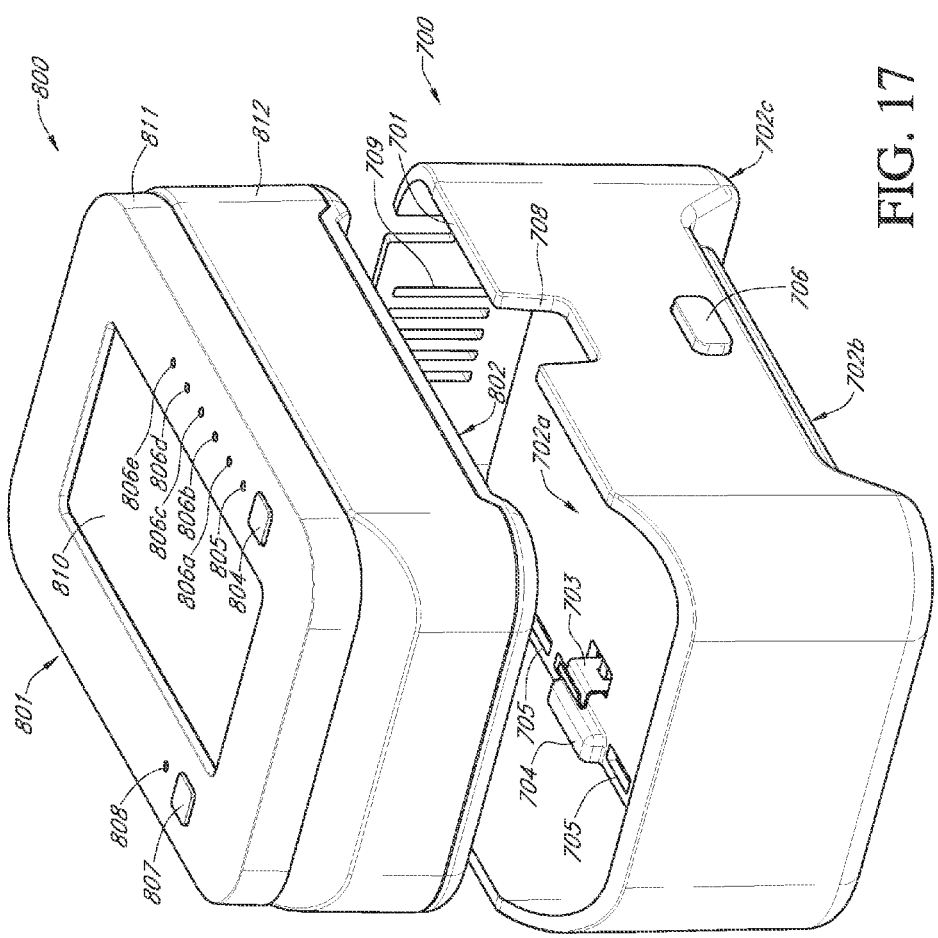

TRANSILLUMINATOR BASE AND SCANNER FOR IMAGING FLUORESCENT GELS, CHARGING DEVICES AND PORTABLE ELECTROPHORESIS SYSTEMS

This application claims benefit of priority to, and is a continuation-in-part of, U.S. patent application Ser. No. 11/764,170, and also claims benefit of priority to, and is a continuation-in-part of, U.S. patent application Ser. No. 11/674,657, now abandoned, and also claims benefit of priority to U.S. Provisional Patent Application 60/773,026, filed Feb. 13, 2006 and U.S. Provisional Patent Application 60/829,513, filed Oct. 13, 2006, the entire contents of all these applications, are incorporated herein by reference in their entireties.

FIELD OF THE INVENTION

The present invention relates to gel electrophoresis systems, particularly gel electrophoresis systems that include gel cassettes and support bases for the cassettes. In some embodiments, the present disclosure relates to charging devices for charging gel electrophoresis systems and to portable gel electrophoresis systems.

BACKGROUND OF THE INVENTION

Fluorescence and transillumination are used in a variety of applications. In the field of fluorescent microscopes, a white light source is used that is passed through an excitation filter, hits the samples, passes through an emission filter and is imaged by either a human eye or camera to view the patterns of labeled biomolecules or natural fluorescence. In the forensic detection field, forensic scientists have used portable fluorescent detection devices since at least the mid 1980's to visualize either natural fluorescence (blood, semen, bacteria, cocaine) or stained fluorescence (DFO for visualization of fingerprints) that rely on a white light source fitted with a blue excitation filter used in combination with an orange filter attached to either a camera or an observers glasses. In the field of underwater fluorescence photography, divers and scientists have been using UV excitation for visualizing and photographing underwater fluorescent organisms and chemicals since the 1950s, but have more recently turned to white light sources with attached blue excitation filter and integrated emission filters on dive masks and camera lenses. In the medical imaging field, exemplary known applications of transillumination include endoscopy devices, dentistry decay detecting devices, and others, all of which generally use a filtered blue light to detect either the autofluorescence of tissue or bacteria or the stained fluorescence of tissue or bacteria so that the image may be viewed using either colored glasses (for diagnosis or surgery) or a camera with a filtered lens (for documentation). Exemplary endoscopy devices include those disclosed in U.S. Pat. Nos. 4,786,813; 5,507,287; and 5,647,368.

Gel electrophoresis is a group of techniques used by scientists to separate molecules based on physical characteristics such as size, shape, or isoelectric point. This process is widely used and has many applications. For example, it is used to analyze DNA molecules according to their resultant size after being digested by restriction enzymes. It is also used to analyze the products of a polymerase chain reaction (PCR). Typically, it is desirable to visualize and to document the results of the electrophoretic separation test. In this regard, with respect to gel electrophoresis, the use of transillumination and fluorescence in general is widespread. Currently scientists run gels in a separate running base, and then remove the gel for visualization. Often, scientists have to place a unique filter over the gel to visualize the separation of the mixture's components on the gel. Stains are typically used that absorb in the UV range and fluoresce in the visible region (e.g., ethidium bromide). If the analyte molecules fluoresce under ultraviolet light, typically visible background light in the viewing area must be reduced or eliminated to visualize or photograph the stained molecules. In addition, an operator or viewer must protect the skin and eyes from exposure to ultraviolet light, further adding to the inconvenience of imaging the separated molecules.

Another known gel viewer is the SAFE IMAGER™ transilluminator sold by Invitrogen (Carlsbad, Calif.) that uses a visible light source and a first filter between the light source and the stained molecules to block background visible light that is not absorbed by a dye molecule and a second filter between the stained molecules and the viewer to block excitation visible light that is not emitted by the dye used to image the separated molecules. Using a visible light source in combination with filters allows a viewer to visualize stained molecules without the need for protective glasses or clothing.

Invitrogen also provides enclosed mini-gel cassettes called "E-gel®" electrophoresis gels. E-gel® cassettes that contain electrophoresis gels are disclosed in U.S. Pat. Nos. 5,582,702, 5,865,974, and 6,379,516. These cassettes can be inserted into an "E-base™" power supply/cassette holder for running gel electrophoresis. E-gel® cassettes include an ion source for electrophoresis and electrodes within the cassette. Upon insertion of the E-gel® cassette into the E-base™ power supply, electrical contact points connect through the E-base™ power supply to an adapter that can be connected to a power source, such as through an electrical outlet. The E-base™ power supply provides controls and readout displays, as described in U.S. patent application Ser. No. 10/946,472, (U.S. patent application publication 2005/121325) filed Sep. 20, 2004, herein incorporated by reference in its entirety.

SUMMARY OF THE INVENTION

Provided herein in one aspect of the invention is a cassette electrophoresis base configured for holding a cassette that contains an electrophoresis gel during electrophoresis that provides electrical connections for contacting electrodes of the cassette and a power supply for supplying power for electrophoretic separation that is designed to be open below the bottom surface of the cassette. The cassette electrophoresis base can be positioned over a light source during and/or following electrophoresis for viewing separating or separated molecules within the gel that is within the cassette. The power supply in preferred embodiments has programmable settings, such as for electrophoresis time, current, and/or voltage, and in preferred embodiments the polarity of the electrical current can be reversed by means of a manual control, such as a switch or button. In some exemplary embodiments, when a cassette is positioned on the base, the cassette electrophoresis base has a space below the cassette between the lower wall of the cassette and the surface on which the base rests. The base can fit over a light box such that the light source fits in the space beneath the cassette positioned on the base, or a light source of a light source base can be inserted into the space immediately below the cassette.

In some exemplary embodiments of this aspect, the invention provides an electrophoresis system that includes a cassette electrophoresis base and a light source base comprising a light source, in which the electrophoresis base fits over the light box such that when a cassette is positioned on the base, the light source is positioned beneath the cassette during electrophoresis and is able to transilluminate a gel within the cassette before, during, and after electrophoresis while the cassette is in the electrophoresis base. The light source can be any type of light source that directs light upward (toward a cassette positioned on the base). The light emitted by the light source can be of any wavelength range, for example in the UV, visible, or infrared wavelengths, or a combination thereof. In some embodiments, the electrophoresis system can further comprise a cassette that includes a gel, electrodes, and one or more ion sources.

An electrophoresis system as disclosed herein can be provided as a commercial product that includes a cassette electrophoresis base and a light source base, and optionally includes one or more cassettes (preferably comprising a gel), one or more filters, one or more dyes or stains, and/or one or more electrophoresis reagents, including but not limited to: one or more loading dyes, one or more denaturing agents (where a denaturing agent includes, without limitation, a detergent, urea, or formamide), one or more solubilizers (including, without limitation, surfactants and lipids), one or more reducing agents, one or more labeling reagents, and one or more running buffers.

The invention includes methods of separating biomolecules using a cassette electrophoresis base that includes a power supply that is positioned over a light source base, in which the methods include: 1) positioning a cassette that contains a gel on a cassette electrophoresis base of the invention, in which the cassette electrophoresis base is positioned over a light source base, and in which the gel within the cassette includes one or more wells for the loading of sample and the cassette comprises one or more openings that access the wells; 2) loading at least one sample that includes one or more biomolecules in at least one of the one or more wells of the gel, in which either the gel, the sample, or both include at least one fluorophore that is bound to or can bind to at least one biomolecule in the sample to provide at least one stained biomolecule;

3) electrophoretically separating the one or more biomolecules of the at least one sample by turning on the power supply of the cassette electrophoresis base to provide power for electrophoretic separation of biomolecules within the cassette, in which the one or more stained biomolecules can be visualized during and after electrophoretic separation using the light source of the light source base.

Another aspect of the invention is a cassette electrophoresis base configured for positioning and holding a cassette during electrophoresis that provides electrical connections for supplying power for electrophoretic separation and includes an integral light source that directs light toward a surface of a cassette positioned in a cassette base. The light source can be used for viewing stained, colored, or fluorescent biomolecules that electrophoretically migrate in a gel within a cassette positioned on the base. The invention in some embodiments of this aspect is directed to an apparatus for conducting electrophoresis and viewing a pattern of fluorescence emitted by one or more fluorophores present in the gel that is within the cassette. An electrophoresis base that includes an integral light source can be provided with one or more cassettes that may or may not comprise a gel, electrodes, and an ion source for electrophoresis; one or more filters; one or more dyes or stains; and/or one or more electrophoresis reagents, including but not limited to: one or more loading dyes, one or more denaturing agents (where a denaturing agent includes, without limitation, a detergent, urea, or formamide), one or more solubilizers (including, without limitation, surfactants and lipids), one or more reducing agents, one or more labeling reagents, and one or more running buffers.

The invention includes methods of separating biomolecules using a cassette electrophoresis base that includes a power supply and an integral light source, in which the methods include: 1) positioning a cassette that contains a gel on a cassette electrophoresis base of the invention that comprises an integral light source, and in which the gel within the cassette includes one or more wells for the loading of sample and the cassette comprises one or more openings that access the wells; 2) loading at least one sample that includes one or more biomolecules in at least one of the one or more wells of the gel, in which either the gel, the sample, or both include at least one fluorophore that is bound to or can bind to at least one biomolecule in the sample to provide at least one stained biomolecule; 3) electrophoretically separating the one or more biomolecules of the at least one sample by turning on the power supply of the cassette electrophoresis base to provide power for electrophoretic separation of biomolecules within the cassette, in which the one or more stained biomolecules can be visualized during and after electrophoretic separation using the light source of the cassette electrophoresis base.

The present invention in some aspects provides gel electrophoresis systems that include gel cassettes and electrophoresis bases for the cassettes, in which the electrophoresis bases support the cassette during electrophoresis and provide electrical connections for supplying power for electrophoretic separation, and built-in or reversibly fitted transilluminators for viewing the separation of biomolecules in gels during and after electrophoresis. In preferred embodiments, at least a portion of the bottom wall of a gel cassette used in an electrophoresis system is transparent to at least one wavelength of light emitted by a transilluminator built into or fitted to the base. In preferred embodiments, at least a portion of a gel cassette used in a gel electrophoresis system is transparent to at least one wavelength of light in the visible range emitted by a transilluminator built into or fitted to the base that can be absorbed by a dye or label present in the gel enclosed in a gel cassette during electrophoresis. In some embodiments, the gel electrophoresis systems are provided with one or more filters that block transmission of one or more wavelengths of light. In some embodiments, cassettes of the gel systems have an upper wall that blocks transmission of light emitted by the transilluminator that is not absorbed by a dye or label present in the gel enclosed in a gel cassette, and allows transmission of light of the wavelength emitted or reflected by a dye or label in the gel enclosed in the gel cassette.

The present invention in some preferred embodiments relates to a gel electrophoresis system incorporating a visible light transillumination system for viewing a pattern of fluorescence emitted by fluorophores comprising a cassette housing fluorophore-containing material and a base unit to support the cassette during electrophoresis. In these embodiments, the base unit houses a light source having output in the visible wavelength region and a filter placed between the light source and the fluorophores. The cassette comprises a top wall, a bottom wall, and sidewalls defining a chamber. The bottom wall supports the fluorophore-containing material (e.g., gel body, buffer, a matrix within the gel, and/or stained biomolecules) and is capable of transmitting exciting light from the light source. The top wall of the cassette can optionally comprise an emission filter capable of transmitting light of the emitted type from the fluorophores and of preventing transmission of the exciting light from the light source. In alternate embodiments, one or more emission filters can be provided with the gel electrophoresis cassette to placed over the cassette for viewing or imaging the gel, and/or one or more emission filters can be provided in the form of glasses that a viewer can put on to view the gel during or after electrophoresis. The system is constructed and arranged such that patterns of fluorescence emitted by the fluorophores are viewable during electrophoresis.

In some preferred embodiments of cassette electrophoresis systems of the invention, the cassette is configured for electrophoresis of biomolecules such as nucleic acids and proteins, and the chamber is substantially closed during electrophoresis. The cassette has a chamber enclosed by walls defining an electrophoresis area comprising at least one body of gel for facilitating electrophoresis. In a preferred embodiment the top wall comprises an emission filter capable of transmitting light of the emitted type from the fluorophores and of preventing transmission of the exciting light. Electrodes are positioned within the chamber and in electrical contact with the gel. An ion source for providing the ions for electrophoresis is also provided within the cassette. A dye source can be positioned within the body of gel or within the ion source (which can be, for example, a solution or matrix), providing a dye for enabling visualization of the electrophoresis. Alternatively, the biomolecules to be separated in the body of gel can be pre-stained or labeled with one or more dyes, or a dye can be added to a sample buffer to be mixed with the biomolecules to be separated. The gel cassette chamber is preferably substantially closed before, during, and after electrophoresis.

Another aspect of the invention is directed to a visible light photoluminescent imaging system for recording an image of one or more patterns of fluorescence emitted by fluorophores capable of being excited by light of an excitation type and capable of emitting light of an emitted type. The imaging system comprises a light source that produces light, a first optical filter, a second optical filter, and a detector. The first optical filter is positioned between the light source and the fluorophores and is capable of transmitting excitation light, and, preferably filter out at least a portion of the emitted light that is not absorbed by a fluorophore in a gel, blot, plate, or array being imaged. The second optical filter is positioned in optical communication with the fluorophores and is capable of transmitting emitted light from the fluorophores and substantially preventing transmission of the excitation light. The system is constructed and arranged such that patterns of emission from the fluorophores are viewable and recordable by the detector.

In some embodiments, the invention provides an imaging system for gels that includes a light source and detector that are integrated into a base unit that a gel, optionally within a cassette, can be positioned on top of for scanning. In preferred embodiments, one or more optical filters is positioned between the light source and the gel or cassette, and one or more additional filters is positioned between the cassettes and the detector, and light emitted from fluorophores in the gel or cassette is directed to the detector by one or more mirrors. In one embodiment, the light source comprises one or more light emitting diodes. The gel to be imaged preferably comprises biomolecules that are preferably stained, either prior to, during, or after electrophoresis, with one or more fluorophores.

In some embodiments of these aspects, excitatory light is directed upward toward a cassette or gel positioned on the imager base, optionally by means of one or more mirrors, and preferably passes through a filter before illuminating one or more fluorophores in the gel. In these embodiments, light emitted by a fluorophore is preferably directed by one or more mirrors to the detector, and preferably passes through a filter that excludes light not originating from the fluorophore en route to the detector. In some preferred embodiments, one or more filters is also provided above the gel, such that a user can view the gel from above while it is imaged. A filter provided above the gel can be incorporated into the upper wall of the gel cassette, can be placed on top of a gel or gel cassette on the imager base, or can be provided in the form of glasses that the user can wear to view the gel.

A further aspect of the invention is a cassette electrophoresis base as described herein that comprises an integral light source, in which the electrophoresis base also includes a gel imaging function. In these embodiments, a cassette electrophoresis base of the invention is configured to hold a gel cassette during electrophoresis and comprises electrical contacts to contact electrodes of the cassette and a power supply for supplying electrical current for electrophoresis, and further includes a light source positioned below the cassette. During operation, the light source emits light that is directed upward toward a cassette or cassettes positioned on the cassette electrophoresis/imaging base, and, preferably, passes through a filter that filters out at least a portion of the light emitted by the light source that is not of a wavelength that is absorbed by a fluorophore used for staining biomolecules electrophoresed in the gel cassette. The gel can be imaged by means of a detector that can be positioned below the gel cassette. Preferably, light emitted by one or more fluorophores present in the gel cassette passes through at least one filter prior to encountering the detector. In some preferred embodiments the detector comprises a camera or imager that comprises or is electronically linked to a computer that can display the gel image on a viewing screen, store the image, and/or direct printing of the image.

In some preferred embodiments, the gel can be viewed from above by a user during electrophoresis on an electrophoresis/imager base. A user can view stained biomolecules within the cassette during or after electrophoresis with the aid of an additional filter that blocks light that is not emitted by a fluorophore in the gel cassette, where an additional filter can be provided in the upper wall of a gel cassette, as a separate piece that can be positioned between the gel cassette and the viewer, or as glasses that can be worn by the viewer. In some exemplary embodiments in which a detector is positioned below the gel cassette, the gel can simultaneously be imaged by the gel imager, and viewed from above by a user of the apparatus. In some illustrative embodiments, both imaging and viewing can occur during electrophoresis.

In these embodiments, the base unit of the electrophoresis imaging system preferably provides contact points for connecting electrodes of the cassettes to a power source. The light source and detector unit of the base are positioned below the one or more cassettes that are positioned on the base, one or more optical filters is positioned between the light source and the cassette(s), and one or more additional filters is positioned between the cassettes and the detector, and light emitted from fluorophores in the gel cassette is directed to the detector by one or more mirrors. In one embodiment, the light source comprises one or more light emitting diodes. In some embodiments, the fluorophores are provided in a gel cassette.

In some embodiments the present disclosure also describes a charging device that is operable to charge an electrophoresis system of the disclosure to enable electrophoresis to be carried out. In one embodiment, a charging device, has a cradle like configuration and an electrophoresis system of the disclosure may be inserted into the charging device. In some embodiments, a charging device of the disclosure may be used to charge an electrophoresis system in a fashion similar to a docking device.

In some embodiments, the disclosure provides a portable electrophoresis system, wherein electrophoresis may be carried out at a site or a location where there is no electric power supply or during power outages. Electrophoresis systems of the disclosure, including a cassette electrophoresis base as described herein as well as electrophoresis systems that in addition to a cassette electrophoresis base further comprise an integral light source, in which the electrophoresis base also includes a gel imaging function may be used with the charging device of the disclosure to form a portable electrophoresis system. In some embodiments, a charging device and/or the portable electrophoresis system provide the convenience of performing electrophoresis at remote locations and may be useful in diagnostic, forensic and other applications at locations where a natural disaster or situation has caused power outages or at sites of field studies.

In some embodiments, the disclosure describes a connector operable to connect two devices comprising: at least a first end operable to provide connectivity to a first device; at least a second end operable to provide connectivity to a second device; at least one switch connected to the connector operable to removable engage the connector to form a connection with the first device and the second device; wherein the first device is a docking device and the second device is an electrophoresis device and the connectivity is mechanical connectivity. In some embodiments, the connector may be further operable to provide electrical connectivity between the two devices.

BRIEF DESCRIPTION OF THE DRAWINGS

The invention will be more readily understood with reference to the embodiments thereof illustrated in the attached figures, in which:

FIG. 17 depicts a schematic isometric view of a charging device that is operable to charge an electrophoresis base and an electrophoresis base, according to one embodiment of the disclosure;

DETAILED DESCRIPTION OF THE INVENTION

Figure 1:
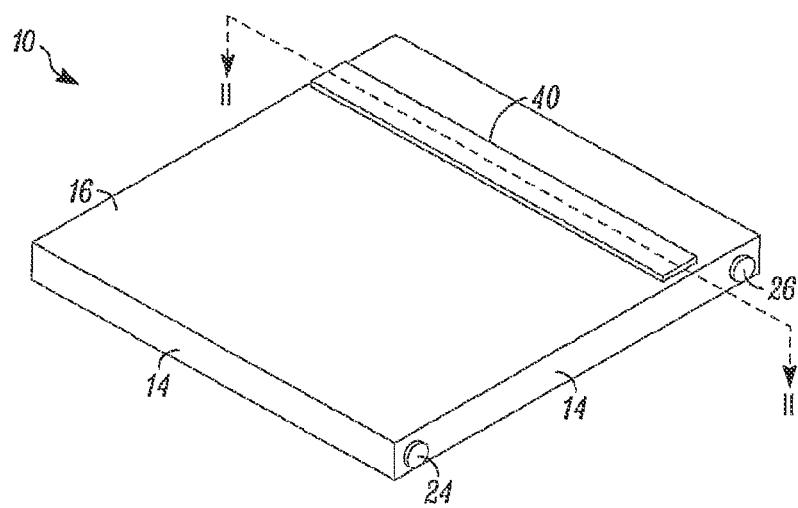
FIG. 1 is a schematic isometric illustration of an electrophoresis cassette, constructed and operative in accordance with one embodiment of the present invention.

Before describing the present invention in detail, it is to be understood that this invention is not limited to specific compositions or process steps, as such may vary. Features of particular embodiments of the invention can be combined to from further embodiments that are also encompassed in the invention.

Unless defined otherwise, all technical and scientific terms used herein have the same meaning as commonly understood by one of ordinary skill in the art to which this invention is related. Generally, the nomenclature used herein and the manufacture or laboratory procedures described below are well known and commonly employed in the art. Where there are discrepancies in terms and definitions used in references that are incorporated by reference, the terms used in this application shall have the definitions given herein. Terms of orientation such as "up" and "down", or "upper" or "lower", "above" and "below" and the like refer to orientation of parts during use of a device. The terms "about" or "approximately" when referring to any numerical value are intended to mean a value of ±10% of the stated value. For example, "about 50° C." (or "approximately 50° C.") encompasses a range of temperatures from 45° C. to 55° C., inclusive. Similarly, "about 100 mM" (or "approximately 100 mM") encompasses a range of concentrations from 90 mM to 110 mM, inclusive. As used in this specification and the appended claims, the singular form "a", "an" and "the" also include plural referents unless the context clearly dictates otherwise. Thus, for example, reference to "a cassette" further includes two or more cassettes and reference to "a fluorophore" includes one or a plurality of fluorphores, etc.

What the human eye perceives as "white light" consists of all the electromagnetic radiation with wavelengths between approximately 400 and 750 nm (the "visible spectrum"). Light from 200-400 nm is called ultraviolet or UV. Different wavelengths of light, when isolated, are seen by the human eye as being colored: light of wavelengths between 400-500 nm is generally seen as violet/blue hues; 500-550 nm is seen as green/yellow hues; and 550-750 nm is seen as orange/red hues. The term "visible light" as used herein refers to light having wavelength(s) between about 400 nm and about 750 nm. Not all wavelengths in this range need to be present in the "visible light" for purposes of this invention.

Many dyes are excited to fluoresce by light within the visible spectrum. However, when white or broad-band visible light is used for excitation of the dye, the fluorescence is not detectable due to the large amount of incident light from the light source itself that reaches the observer or detecting instrument. This problem is overcome by placing suitable optical filters on either side of the material to which the fluorophore is bound to prevent the totality of the lamp light from reaching the observer and allow the fluorescent light from the fluorophore to be seen.

"Optical filters" remove by "absorbing" or "reflecting" i.e., prevent transmission of, light of a certain type while allowing the passage or "transmittance" of light of another type. For example, a color filter that appears blue is absorbing most of the green and red light and transmitting the blue light. A color filter that appears amber is absorbing blue light and transmitting green and red light. The combination of green and red light appears yellow-orange to the eye, giving the filter a yellow-orange or amber color.

The exact optical properties of a color filter are due to the light absorption properties of the particular pigments embedded in its matrix. The filter matrix itself may be made from a wide range of materials known to the art and available to the skilled worker including plastics, such as acrylics, gelatin, and glass.

Another type of filter is a dichroic mirror. A dichroic mirror is a semi-transparent bandpass filter that reflects light shorter than a specific wavelength and transmits light that is longer than that wavelength.

Another type of optical filter is a polarizing filter. A polarizing filter transmits light of only a narrow range of orientations and prevents transmission of light of other orientations. The optical properties of filters are measured in terms of either the "absorbance" or "percent transmittance.

"Fluorescence" is the phenomenon in which light energy ("exciting light") is absorbed by a molecule resulting in the molecule becoming "excited." (Lakowicz, J. R. (1983) "Principles of Fluorescence Spectroscopy," Plenum Press, New York.) After a very brief interval, the absorbed light energy is emitted by the excited molecule, usually at a longer wavelength than the exciting light. This emitted light is referred to as fluorescent light. A molecule that exhibits fluorescence is referred to as a "fluorophore." Any given fluorophore will be excited to fluoresce more by some wavelengths of light than other wavelengths. The relationship between wavelengths of light and degree of excitation of a given fluorophore at that wavelength is described by the "excitation spectrum" of the fluorophore. The excitation spectrum is also called the "excitation wavelength range" herein.

Typical fluorophores include many organic dyes. However, most molecules of biological origin such as nucleic acids, proteins, lipids and coenzymes are not strongly fluorescent. (Notable exceptions include certain fluorescent proteins such as phycobiliproteins, Green Fluorescent Protein, DsRed, and their derivatives and various pigments such as chlorophyll and others used for coloration of plants and animals.) Therefore, to detect biological molecules it is usually necessary to either stain or react a biological sample with a fluorophore. "Staining" usually refers to the process in which a fluorescent dye binds relatively weakly to a target molecule without the formation of covalent bonds. If a fluorophore is "reacted" with a target molecule, this usually implies that the complex between the two species involves a relatively robust covalent bond. As used herein, however, "staining" is used to refer to relatively weak and general binding of a dye to a molecule or class of molecules, and is also used to refer to conjugation of a dye or label to a biomolecule by means of reactive groups on the dye or label and biomolecule. A stained biomolecule electrophoresed or imaged using the devices and methods of the invention can be any type of biomolecule, including, without limitation, a peptide, protein (proteins and peptides include, without limitation, glycoproteins, lipoproteins, and proteins and peptides comprising natural or non-natural modifications including the addition of chemical groups or moieties), nucleotide, nucleic acid (nucleotides and nucleic acids includes non-natural or substituted nucleotides and nucleic acids, for example, peptide nucleic acids, locked nucleic acids, nucleic acids comprising sugars other than ribose and deoxyribose, nucleotides and nucleic acids having derivatized, modified, or labeled bases or sugars, etc.), sugars, carbohydrates, lipids, fatty acids, and sterols.

A biomolecule can be stained or labeled using any staining, labeling or conjugation techniques. In one example, a dye (such as, for example, a SYBR® dye for nucleic acid staining) is provided in a cassette, for example, in an ion reservoir, running buffer, and/or within the gel, and biomolecules are stained with the dye during electrophoresis. In another example, a dye that stains biomolecules is provided in a sample loading buffer, which is optionally pre-incubated with a sample before it is loaded on the gel. In yet another example, chemical conjugation techniques are used to attach a dye, such as a fluorophore, to one or more specific biomolecules or a class of biomolecules present in a sample, for example. Biomolecules can also be labeled metabolically in cells, tissues, or organisms. An extensive body of information on and protocols for labeling of biomolecules is available in the scientific literature and in various manuals (for example Richard P. Haugland, MOLECULAR PROBES HANDBOOK OF FLUORESCENT PROBES AND RESEARCH CHEMICALS (10th edition, CD-ROM, September 2005; available at Invitrogen.com).

A sample that comprises one or more biomolecules to be electrophoretically separated can be any kind of sample, including but not limited to, a cell lysate, a cell fraction, a reaction product, or one or more partially purified or substantially purified biomolecules.

In order to visualize or produce an image of a fluorophore, a filter pair can be used that comprises a first filter positioned between the light source and the fluorophore that transmits light of the excitation wavelength but blocks at least a portion of the light that is not of the excitation wavelength and a second filter that is positioned between the fluorophore and the viewer, detector, or camera that transmits light of the wavelength emitted by the fluorphore and preferably blocks transmission of at least a portion of the light that is not of the emitted wavelength.

In one example, a fluorophore that is maximally excited at around 500 nm or less (i.e., by blue light) and emits its maximum fluorescence at 500 nm or more (e.g., the fluorescence is green or red) is used to detect biomolecules electrophoreses in gels. In these exemplary embodiments, a first filter, which is blue, is placed between the light source and the fluorophore and absorbs the green and red components of the visible light and transmits only blue light through to the fluorophore. The blue light excites the fluorophore to fluoresce. Between the fluorophore and observer is placed a second filter, which is amber, that absorbs the blue light from the light source but transmits the green or red fluorescent light from the fluorophore to the light detector, e.g., a human viewer or detection equipment.

The term "light source" is any device capable of emitting ultraviolet (UV) or visible light e.g., a typical household light such as a low-powered fluorescent tube or incandescent bulb that produces visible light including wavelengths within the excitation spectrum of the fluorophore, a xenon lamp, a mercury lamp, a deuterium lamp, a tungsten-halogen lamp, or one or more light emitting diodes (LEDs), or lasers, such as, for example, Krypton or Argon lasers. A light source can include more than one element that produces light, for example, more than one bulb, filament, tube, lamp, laser, or diode. Preferred light sources are those that emit light in the visible range, such as incandescent, fluorescent, or LED light sources. LED light sources can be selected for emission spectra that correspond to the absorption spectra of fluorphores used to stain the biomolecules to be electrophoresed. For example, LEDs that emit light primarily in the blue wavelengths ("blue light LEDs") can be used as a light source for many fluorophores that absorb at wavelengths at or below about 500 nm.

The invention provides cassette-based electrophoresis systems that comprise an electrophoresis cassette base as described herein, and a gel cassette that fits the cassette base, such that when the gel cassette is positioned on the base, electrodes of the cassette are in electrical contact with the base, which serves as a power supply for electrophoresis through a gel within the cassette. A gel cassette, or, herein, simply a "cassette" comprises a body of gel (or simply, "a gel") for separating biomolecules, at least two electrodes, and at least one ion source, in which at least a portion of the bottom wall of the cassette is transparent to at least one wavelength of light emitted by the light source of the cassette base, or engaged with the cassette base, and at least a portion of the top wall of the cassette absorbs at least one wavelength of light emitted by the light source of the cassette base. The cassette-based electrophoresis system is configured such that when a cassette is positioned on the base each of the electrodes of the cassette contacts an electrical contact point of the base, and light from a light source of the base, or engaged with the base, is directed upward from below the bottom surface of the cassette into the body of a gel within the cassette.

A preferred embodiment is an electrophoresis system provided herein in which molecules can be visualized during there electrophoretic separation that includes a cassette that is substantially closed before, during, and after electrophoresis, allowing for electrophoresis to occur in a self-contained unit that can be inserted into the electrophoresis cassette base and removed from the base without having to disconnect leads or tubing, remove the cassette from a buffer chamber or disconnect a one or more buffer chambers, with all the attendant mess and inconvenience. The substantially closed cassette includes at least one body of gel for separating biomolecules, at least one ion source for driving electrophoresis, and at least two electrodes positioned at opposite ends of the gel for establishing a potential difference across the gel during electrophoresis. In this regard, the substantially closed cassette is an "all-in-one" or "ready-to-run" electrophoresis cassette in that after loading of a sample on the gel within the cassette, the cassette need only be attached to a power supply to conduct electrophoretic separation. No further reagents, devices, or structures are required. An electrode positioned within the cassette at one end of the body of gel serves as a cathode during electrophoresis, and an electrode positioned within the cassette at one end of the body of gel serves as an anode during electrophoresis. The electrodes may be wire, rods, or mesh of any suitable conductive material, such as metal (for example, stainless steel, platinum, aluminum, lead, silver, copper) or conductive nonmetals, such as carbon, for example. Electrodes may be constructed of a nonconductive material coated with or otherwise combined with a conductive material. Ends of each electrode are exposed to the outside of the cassette to make contact with the electrical contact points of the electrophoresis cassette base.

"Substantially closed" means that the gel within the cassette is surrounded by the walls of the cassette, although there may be openings in one or more cassette walls for loading of wells in the gel and, optionally, for release of gases that may be generated in the area of the electrodes during electrophoresis. Openings that may be present for the loading of samples into wells can be covered prior to electrophoresis, for example, by a removable cap, lid, or sticker, or by a comb inserted into the wells that is removed just prior to loading of samples on the gel for electrophoresis. A substantially closed cassette can remain closed for removal of the cassette and enclosed gel from the base after electrophoresis, but can, in some embodiments, be opened at a later time for removal of the gel from the cassette.

Electrophoresis is typically accomplished by electrolysis of water at the electrodes, leading to the evolution of oxygen gas at the anode and hydrogen gas at the cathode. Strategies for reducing, avoiding, or accommodating gas evolution at the electrodes (and the need for an open cassette) are disclosed, for example, in U.S. Pat. Nos. 5,582,702, 5,865,974, and 6,379,516, and U.S. Patent Application Publication 20020112960, all herein incorporated in their entireties. The cassettes of the present invention can use any of these designs, or others, in any combination.

In some embodiments, an electrochemically ionizable metal, such as copper, silver, or lead, can be used for one or both electrodes. Another strategy for enabling closed-cassette electrophoresis is through the use of electrodes that comprise metals that absorb molecular hydrogen or oxygen, such as palladium or aluminum, respectively, or to include metal salts that absorb hydrogen or oxygen in the vicinity of the cathode and anode. In other aspects, one or both electrode regions of the cassette can comprise one or more small vent holes, such as in the upper wall of the cassette, for venting gases. For example, a cassette used in an electrophoresis system of the invention can also have one or more small vent holes in the area of one or both electrodes for venting the gases produced during electrophoresis. Vent holes that may be present in regions of the cassette near an electrode typically are less than about 3 mm in diameter, and can be less than about 2 mm in diameter, for example, 1 mm in diameter or less. Vent holes, when present, can be covered with a removable sticker, lid, or cap that is removed prior to electrophoresis.

The cassette includes at least one ion source for driving electrophoresis that can be provided in any form, for example, as a solution (such as a buffer solution) at one or both ends of the gel, as a (such as, for example, an ion-loaded ion exchange matrix) at one or both ends of the gel, or as a sparingly soluble salt provided at one or both ends of the gel (see, for Example, U.S. published Application 20020134680, U.S. Pat. No. 5,582,702, U.S. Pat. No. 5,865,974, U.S. Pat. No. 6,379,516, and U.S. Published Application 20020112960, all herein incorporated in their entireties). A cassette can have, for example, a buffer solution ion source at the cathode end of the gel in electrical contact with the cathode and a matrix including an ion source at the anode end of the gel in electrical contact with the anode, or any combination of feasible ion sources at one or both of the anode and cathode ends.

A cassette of an integrated gel electrophoresis/viewing system presented herein has a bottom wall and a top wall. The cassette also has side walls, although the side walls at the edges of the cassette may be formed by fusing or adhering spacers between the bottom and top walls or by fusing or adhering the borders of the bottom and top wall. The bottom wall of a cassette transmits light emitted by the light source of the base that is of a wavelength can be used to excite one or more dyes or labels used in electrophoresis. In some embodiments the bottom wall of the cassette does not transmit most visible wavelengths of light that are not absorbed by dyes or stains used in electrophoresis, so as to reduce background light when viewing the gel. The top wall of the cassette is transparent to wavelengths of light emitted by a fluorophore dye or label used in electrophoresis. In some embodiments, the top wall of the cassette does not transmit light of the wavelength range that passes through the bottom wall of the cassette to excite a fluorophore in the gel. A cassette can is some embodiments therefore be designed for use with a dye or dyes to be used in electrophoresis, where the one or more dyes are either provided in the cassette (in the body of gel or ion source, for example) or with sample(s) to be loaded on the gel, and for use with an electrophoresis base that includes or engages a light source that emits light at appropriate wavelength for exciting fluorophores used in the electrophoresis.

The dimensions of the cassette are not limiting to the invention. For example, a cassette can be a "mini-gel" cassette of about 8 cm×about 6 cm (length×width) or less in either dimension, or about 10 cm×about 8 cm or less in either dimension, or by about 9.5 cm×about 7.5 cm, or by about 10.5 cm×about 13.5 cm, or by about 15 cm×about 10 cm, or by about 20 cm×about 15 cm, or by about 20 cm×about 15 cm, or greater in either dimension. The thickness of the internal space (i.e., the gel width) can be about 1 cm or less, or about 5 mm or less, or about 2 mm or less, or about 1 mm or less. A cassette power supply base that includes an illuminator will be configured to accommodate one or more cassettes, having dimensions that allow a cassette to be positioned over a light source and connect to electrical contact points.

An electrophoresis system as described herein, such as an electrophoresis cassette base that includes a power supply and reversibly engages a light source base, or, in another embodiment provided herein, an electrophoresis cassette base that includes a power supply and integral light source, can also include a gel imager that can fit over the electrophoresis cassette base. For example, a camera unit or electronic imaging unit can be fitted over a cassette as it is positioned in the base to take a photograph (such as but not limited to a digital photograph) or to create an image of the gel that can be directly stored, displayed on a screen, or printed. The imaging unit can optionally store or download images into a documentation program that allows the user to enter information about the sample(s) run on the gel, the gel, and/or the electrophoresis conditions.

The following description of light sources, filters, dyes, stains, labels, fluorophores, cassettes, gels, electrodes, electrophoresis, and detection of biomolecules can be applied to aspects of the invention in which a light source is not integral to a cassette electrophoresis base as well as to aspects of the invention in which a light source is integral to a cassette electrophoresis base. It is understood as well that features of various embodiments of the invention can be combined to create further embodiments that are within the scope of the invention.

A UV light source can be for example, a xenon lamp or deuterium lamp. A visible light source can be, for example, one or more incandescent bulbs, one or more fluorescent bulbs, one or more xenon lamps, one or more mercury lamps, one or more tungsten-halogen lamp, one or more lasers, or one or more LEDs.

Due to the hazards and inconvenience of using UV, including the natural property of most plastics to not transmit UV light, visible light sources are preferred for the electrophoresis cassette base. The term "visible light" as used herein refers to light having wavelength(s) between about 400 nm and about 750 nm. The light source can emit a broad spectrum of visible light, or a visible light source can emit light of any range of wavelengths in the visible range, for example from 400-500 nm (violet/blue), from 500-550 nm (green/yellow), and from 550-750 nm (orange/red) hues.

In some exemplary embodiments, LEDs are used as a light source. In an illustrative example, blue light emitting LEDs can be used as the light source. An LED light source can include any number of LEDs, for example, from one to 1,000 LEDs, such as from two to 800 LEDs, from four to 600 LEDs, from six to 400 LEDs, or from eight to 200 LEDs. For example, a light box can comprise a light source having from one to fifty, one to ten, ten to twenty, twenty to forty, fifty to 100, forty to sixty, sixty to eighty, eighty to 100, 100 to 300, 100 to 150, 150 to 200, 200 to 300, 200 to 600, 300 to 400, 400 to 500, 500 to 750, or 750 to 1000 LEDs.

In some exemplary embodiments of light source bases that are dimensioned to fit beneath a cassette of dimensions ranging from about 5 cm (length) by 3 cm (width) to about 20 cm (length) by about 15 cm (width), a light source base can include, for example, an array of two, three, four, five, six, seven, eight, nine, ten, eleven, twelve, thirteen, fourteen, fifteen, sixteen, seventeen, eighteen nineteen, twenty, between twenty and twenty-five, between twenty-five and thirty, between thirty and thirty-five, between thirty-five and forty, between forty and forty-five, between forty five and fifty, between fifty and sixty, between sixty and seventy, between seventy and eighty, between eighty and ninety, between ninety and one hundred, between 100 and 125, between 125 and 150, between 150 and 200, between 200 and 250 LEDs. For example, an array of LEDs in a light source base can include two, three, six, eight, ten, twelve, fifteen, sixteen, eighteen, twenty, twenty-four, thirty-six, forty-eight, sixty-four, seventy-two, ninety-six, 108, 112, 124, 148, or more LEDs. The LEDs can be arranged in any pattern or configuration that provide illumination of a fluorophore within a cassette positioned over the light source base. The arrangement of LEDs of the light source base can be optimized to produce uniform and sufficiently bright illumination across the area of a cassette placed over the light source base.

The light source base can also optionally include a diffusion filter that can be integrated into the surface of the light source base that light passes through before illuminating a sample such as a gel within a cassette, a membrane, a slide, or a dish that includes molecules stained with one or more fluorophores. In an alternative, a diffusion filter can placed over the light source base so that it is positioned between the light source and the sample to be illuminated. Illumination from the light source base to a cassette, membrane, slide, or plate positioned over a light source base can be made more uniform across a wider area when a diffusion filter of an opaque material is used, such as, for example, frosted glass, a white acrylic sheet, an acetal filter, a mylar sheet, and white opaque plastics. A diffusion filter can range in thickness, for example from about 0.2 mm to about 6 mm. The distance from the filter to the light source can range, for example, from about 2.5 mm to about 50 mm.

The light source can include LEDs that emit light of different wavelength that are separately controlled, such that particular wavelength emitting LEDs can be used for particular fluorophores. For example, white, ultraviolet, near ultraviolet, blue, bluish-green, green, yellow, orange, orange-red, red, and infrared light emitting LEDs can be used made of materials such as but not limited to aluminum nitride, aluminum gallium nitride, diamond, silicon, sapphire, zinc selenide, silicon carbide, indium gallium nitride, gallium nitride, gallium phosphide, gallium arsenide phosphide, aluminum gallium indium phosphide, aluminum gallium phosphide, aluminum gallium arsenide, and gallium nitride. The LEDs used in a light source base can be of any size or shape. LEDs can be any type LED, for example, high powered LEDs, surface mount technology (SMT) LEDs, including SMT micro LEDs, or high flux (or "superflux") LEDs, and can range in power from, for example, about 10 mAmp to about 500 mAmp, or from about 20 mAmp to about 400 mAmp. The LEDs used in the light source base can be bin selected or not bin selected.

Preferably, the light source can be controlled by the user such as by a switch, button, or dial on the electrophoresis cassette base that can be used to turn the light on or off. The control switch, button, or dial can in some embodiments be used to turn the light source on for a set period of time, for example, for a period of time from about ten seconds to about twenty minutes, such as for ten, fifteen, twenty, thirty, forty-five, or sixty seconds, or for one, one and a half, two, three, four, five, six, seven, eight, nine, ten, twelve, fifteen, seventeen, eighteen, twenty, or more than twenty minutes. The light source can be on as a gel within a cassette positioned on the base is running, allowing the operator to monitor the separation of stained biomolecules during electrophoresis.

A light source base or integrated electrophoresis base with light source can include one or more fans to provide cooling in the area of the light source. The light source base or integrated electrophoresis-light source base can include one or more temperature sensors and/or thermocouples that can detect temperature, and preferably cause a warning light or sound and/or cause automatic shut-off of the light source, when temperature rises above a certain level (for example, 35, 40, 45, 50, 55, 60, 65, or 70, or 75 degrees centigrade).

In preferred embodiments, the light source emits visible light that can transmit through the bottom of the cassette, although it is not required that the light source itself be directly below the cassette. In some embodiments, as the emitted light can be directed, for example, by one or more mirrors, from a light source angled away from the cassette (either above, even with, or below the level of the cassette) up through the lower wall of the cassette. In some embodiments, light emitted from fluorophores in the cassette can be directed to a detector by means of one or more mirrors.

The dyes, stains, or labels, generally referred to as reporter molecules, used to detect biomolecules in gels can be any that absorb light energy in the wavelengths emitted by a light source (preferably, but not exclusively, in the visible range) and emit light in the visible range that is sufficiently intense to be visibly detectable, and which associate either directly or indirectly with a desired analyte. A dye or stain can be provided within the body of gel of the gel within a cassette, can be provided within a buffer or other solution or ion source provided within a cassette, such as, for example, a matrix, where the dye can stain one or more biomolecules after they are applied to the gel. Alternatively, a sample to be electrophoresed can be mixed with one or more dyes or stains prior to electrophoresis, in which the one or more dyes or stains can covalently or noncovalently bind one or more biomolecules in the sample. One or more biomolecules can optionally be covalently labeled with a dye, stain, or label prior to electrophoresis, for example.

The term "reporter molecule" as used herein refers to any luminescent molecule that is capable of producing a visible signal when associated with an analyte, either directly or indirectly. Included are reporter molecules typically used in a fluorometer for detection of an analyte such as nucleic acid and proteins. Reporter molecules that are presently commercially available include, but are not limited to, SYPRO® protein stains, PICOGREEN® nucleic acid dye, Deep Purple protein stain, SYTO® nucleic acid dyes, SYBR® dyes, SYBR® Safe nucleic acid stain, Flamingo® dyes, Coomassie Fluor™ dyes, and Lucy® dyes. Typically, luminescent molecules, as used herein include dyes, fluorescent proteins, phosphorescent dyes, chromophores, enzyme substrates, haptens and chemiluminescent compounds particles, haptens, enzymes and their colorimetric, fluorogenic and chemiluminescent substrates that are capable of producing a detectable signal upon appropriate activation. The term "dye" refers to a compound that emits light to produce an observable detectable signal. "Dye" includes fluorescent and non-fluorescent compounds that include without limitations pigments, fluorophores, chemiluminescent compounds, luminescent compounds and chromophores. The term "chromophore" as used herein refers to a label that emits and/or reflects light in the visible spectra that can be observed without the aid of instrumentation. The term "fluorophore" as used herein refers to a composition that is inherently fluorescent or demonstrates a change in fluorescence upon binding to a biological compound, i.e. can be fluorogenic or the intensity can be diminished by quenching. Fluorophores may contain substitutents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a benzazole, a borapolyazaindacene and xanthenes including fluoroscein, rhodamine and rhodol as well as other fluorophores described in Richard P. Haugland, MOLECULAR PROBES HANDBOOK OF FLUORESCENT PROBES AND RESEARCH CHEMICALS (10th edition, CD-ROM, September 2005; available at invitrogen.com).

In certain embodiments the reporter molecule is a dye or label that is conjugated to a specific binding partner, wherein the specific binding partner binds to the analyte or a molecule covalently attached to the analyte. The term "label" as used herein refers to a chemical moiety or protein that retains it's native properties (e.g. spectral properties, conformation and activity) when attached to a labeling reagent and used in the present methods. The label can be directly detectable (fluorophore) or indirectly detectable (hapten or enzyme). Such labels include, but are not limited to, pigments, dyes or other chromogens that can be visually observed, imaged, or measured with a detector; and fluorescent labels (fluorophores), where the output signal is generated by the excitation of a suitable molecular adduct and that can be visualized by excitation with light that is absorbed by the dye or can be measured with standard fluorometers or imaging systems, for example. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term label can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidase (HRP) to bind to the tag, and then use a colorimetric substrate (e.g., tetramethylbenzidine (TMB)) or a fluorogenic substrate such as Amplex Red reagent (Molecular Probes, Inc.) to detect the presence of HRP. Numerous labels are know by those of skill in the art and include, but are not limited to, particles, fluorophores, haptens, enzymes and their colorimetric, fluorogenic and chemiluminescent substrates and other labels that are described in Richard P. Haugland, MOLECULAR PROBES HANDBOOK OF FLUORESCENT PROBES AND RESEARCH PRODUCTS (10th edition, CD-ROM, September 2005), supra.

Typically the label would be an antibody, antigen, biotin or streptavidin, all conjugates typically used in an immunoassay. However, there is no intended limitation of the specific binding partner that can be conjugated to a label and used in the present methods to detect a target analyte. Representative nonlimiting examples of specific binding pairs include: antigen-antibody, biotin-avidin (or streptavidin), IgGProtein A or Protein G, drug-drug receptor, folate-folate binding protein, toxin-toxin receptor, carbohydrate-lectin, peptide-peptide receptor, protein-protein receptor, enzyme substrate-enzyme, iron-iron chelators, hormone-hormone receptor.

The labels of the present invention include any directly or indirectly detectable label known by one skilled in the art that can be covalently attached to a specific binding partner. Labels include, without limitation, a chromophore, a fluorophore, a fluorescent protein, a phosphorescent dye, a tandem dye, a particle, a hapten, an enzyme, and a radioisotope. Preferred labels include fluorophores, fluorescent proteins, haptens, and enzymes.

A fluorophore of the present invention is any chemical moiety that exhibits an absorption maximum beyond 280 nm, and when covalently attached to a labeling reagent retains its spectral properties. The conjugation to the analyte can happen after immobilization on a gel or prior to immobilization. Fluorophores of the present invention include, without limitation; a pyrene (including any of the corresponding derivative compounds disclosed in U.S. Pat. No. 5,132,432), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine (including any corresponding compounds in U.S. Ser. Nos. 09/968,401 and 09/969,853), a carbocyanine (including any corresponding compounds in U.S. Ser. Nos. 09/557,275; 09/969,853 and 09/968,401; U.S. Pat. Nos. 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; and publications WO 02/26891, WO 97/40104, WO 99/51702, WO 01/21624; EP 1 065 250 A1), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774, 339; 5,187,288; 5,248,782; 5,274,113; and 5,433,896), a xanthene (including any corresponding compounds disclosed in U.S. Pat. Nos. 6,162,931; 6,130,101; 6,229,055; 6,339, 392; 5,451,343 and U.S. Ser. No. 09/922,333), an oxazine (including any corresponding compounds disclosed in U.S. Pat. No. 4,714,763) or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

When the fluorophore is a xanthene, the fluorophore is optionally a fluorescein, a rhodol (including any corresponding compounds disclosed in U.S. Pat. Nos. 5,227,487 and 5,442,045), or a rhodamine (including any corresponding compounds in U.S. Pat. Nos. 5,798,276; 5,846,737; U.S. Ser. No. 09/129,015). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171). Alternatively, the fluorophore is a xanthene that is bound via a linkage that is a single covalent bond at the 9-position of the xanthene. Preferred xanthenes include derivatives of 3H-xanthen-6-o13-one attached at the 9-position, derivatives of 6-amino-3H-xanthen-3-one attached at the 9-position, or derivatives of 6-amino-3H-xanthen-3-imine attached at the 9-position.

Preferred fluorophores of the invention include xanthene (rhodol, rhodamine, fluorescein and derivatives thereof) coumarin, cyanine, pyrene, oxazine and borapolyazaindacene. Most preferred are sulfonated xanthenes, fluorinated xanthenes, sulfonated coumarins, fluorinated coumarins and sulfonated cyanines. The choice of the fluorophore attached to the specific binding partner will determine the absorption and fluorescence emission properties of the reporter molecule and subsequent selection of the ASE. Physical properties of a fluorophore label include spectral characteristics (absorption, emission and stokes shift), fluorescence intensity, lifetime, polarization and photo-bleaching rate all of which can be used to distinguish one fluorophore from another.

Typically the fluorophore contains one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

In some preferred aspects of the invention, a fluorophore used to label a molecule is not a naturally occurring amino acid, for example, preferably a fluorophore used for detection of biomolecules is not tryptophan or tyrosine, which can exhibit weak fluorescence. In one aspect of the invention, the fluorophore has an absorption maximum beyond 480 nm. In a particularly useful embodiment, the fluorophore absorbs at or near 488 nm to 514 nm (particularly suitable for excitation by the output of the argon-ion laser excitation source) or near 546 nm (particularly suitable for excitation by a mercury arc lamp).

Fluorescent proteins may also find use as labels in the present invention. Examples of fluorescent proteins include green fluorescent protein (GFP) and the phycobiliproteins and the derivatives thereof. The fluorescent proteins, especially phycobiliproteins (for example, phycoerythrin, phycocyanin, allophycocyanin, and other phycobiliproteins and derivatives thereof), are particularly useful for creating tandem dye labeled labeling reagents. These tandem dyes comprise a fluorescent protein and a fluorophore for the purposes of obtaining a larger stokes shift wherein the emission spectra is farther shifted from the wavelength of the fluorescent protein's absorption spectra. This is particularly advantageous for detecting a low quantity of a target in a sample wherein the emitted fluorescent light is maximally optimized, in other words little to none of the emitted light is reabsorbed by the fluorescent protein. For this to work, the fluorescent protein and fluorophore function as an energy transfer pair wherein the fluorescent protein emits at the wavelength that the fluorophore absorbs at and the fluorophore then emits at a wavelength farther from the fluorescent proteins than could have been obtained with only the fluorescent protein. A particularly useful combination is the phycobiliproteins disclosed in U.S. Pat. Nos. 4,520,110; 4,859,582; 5,055,556, and the sulforhodamine fluorophores disclosed in U.S. Pat. No. 5,798,276, or the sulfonated cyanine fluorophores disclosed in U.S. Ser. Nos. 09/968/401 and 09/969/853; or the sulfonated xanthene derivatives disclosed in U.S. Pat. No. 6,130,101, and those combinations disclosed in U.S. Pat. No. 4,542,104. Alternatively, the fluorophore functions as the energy donor and the fluorescent protein is the energy acceptor.

In another embodiment the reporter molecules are fluorgenic wherein they become fluorescent when associated with the analyte. Such reporter molecules include dyes that associate with nucleic acid (DNA and/or RNA), proteins (total and subsets such as post-translationaly modified proteins), pH, and metal ions. Reporter molecules for the detection of nucleic acid typically include unsymmetrical cyanine compounds, either monomers or dimmers, including, but not limited to compounds disclosed in U.S. Pat. Nos. 4,957,870; 4,883,867; 5,436,134; 5,658,751; 5,534,416; 5,863,753; 5,410,030; 5,582,977; 6,664,047; U.S. Ser. Nos. 10/911,423; 11/005,860; 11/005,861; 60/680,243 and WO 93106482; ethidium dimers (U.S. Pat. No. 5,314,805), acridine dimers and acridine-ethidium heterodimers (U.S. Pat. No. 6,428,667 and Rye, et al. Nucleic Acids Research (1990) 19(2), 327). The following references describe DNA intercalating fluorescent dimers and their physical characteristics: Gaugain et al., Biochemistry (1978) 17:5071-5078; Gaugain et al., Biochemistry (1978) 17:5078-5088; Markovits et al., Anal. Biochemistry (1979) 94:259-269; Markovits et al. Biochemistry (1983) 22: 3231-3237; and Markovits et al., Nucl. Acids Res. (1985) 13:3773-3788. Commercially available dyes include ethidium bromide, acridine orange, Pyronin Y, DAPI, Hoescht stains (such as but not limited to Hoescht 33342 and Hoescht 33258), JOJOTM-1 iodide, YOYO®-1 iodide, SYTO® nucleic acid stains (e.g,), SYTOX® nucleic acid stains (e.g., SYTOX® red, SYTOX® blue, or SYTOX® green nucleic acid stains), SYBR® Green I nucleic acid stain, SYBR® Green II nucleic acid stain, SYBR® Safe nucleic acid stain, SYBR® Gold nucleic acid stain, SYBR® 555 nucleic acid stain, PICOGREEN® nucleic acid stain, RIBOGREEN® RNA reagent and OLIGREEN® nucleic acid stain (Invitrogen Corp., Carlsbad, Calif.). Particularly useful in the context of the present invention are the SYBR® dyes for nucleic acid detection that absorb in the visible light range such as, for example, SYBR® Green I, SYBR® Green II, SYBR® Safe, and SYBR® Gold. Nucleic acid molecules to be electrophoresed using a system of the present invention, such as for example, nucleic acid molecular weight markers, can also be covalently labeled with one or more fluorescent labels.

In another embodiment the reporter molecules stain proteins, either directly or by forming a ternary complex comprising a metal ion. Such reporter molecules include, but are not limited to those disclosed in U.S. Pat. No. 5,616,502; U.S. Ser. Nos. 11/241,323; 11/199,641; 11/063,707; 10/966,536; 10/703,816; and 6,967,251. Commercially available protein stains include SYPRO® Ruby total protein stain, SYPRO® Orange protein stain, SYPRO® Red proteins stain, SYPRO® Tangerine protein stain, Pro Q® Emerald glycoprotein stain, Pro Q® Diamond Phosphoprotein stain, Pro Q® Amber transmembrane stain, Pro Q® Sapphire his tagged protein stain, NanoOrange® protein stain, and Coomassie Fluor™ orange protein stain (Invitrogen Corp., Carlsbad, Calif.). The SYPRO® dyes and Pro Q® dyes referred to herein are particularly useful in the context of the invention for their activation by visible light, as are the SYTO® dyes for the staining of blotted proteins. For example, protein molecular weight markers can be stained with one or more dyes or labels prior to performing gel electrophoresis using a cassette-based integrated system described herein. Progress of the electrophoresis can be monitored in real time by observing the separation of the pre-labeled molecular weight markers running on the gel.

A dye or stain can be provided in a cassette (for example, in the gel, buffer, or ion source) or can be present in a sample to be electrophoresed.

Nonlimiting examples of dyes that can be used with a blue light source include SYBR® Green I, SYBR® Green II, SYBR® Safe, and SYBR® Gold for nucleic acids, and SYPRO® Ruby, SYPRO® Tangerine, SYPRO® Orange, Pro Q® Diamond, and COOMASSIE FLUOR™ Orange for proteins.

In one aspect, the invention provides a cassette electrophoresis base configured for holding a cassette during electrophoresis that provides electrical connections for supplying power for electrophoretic separation and also includes a power supply. In these aspects of the invention, a cassette electrophoresis base is configured such that when a cassette is positioned in the base, the base is open below the bottom surface of the cassette, such that light can be directed upward from a light source into the cassette. The entire cassette electrophoresis base can be positioned over a light source during or following electrophoresis for viewing separating or separated molecules within the gel that is within the cassette without removing the cassette from the base. Preferably, when a cassette is positioned in the cassette electrophoresis base, the height of the space beneath the cassette, from the bottom-most surface of the base (in the region of the base that supports the cassette at one or more edges of the cassette) to the bottom surface of the cassette, is less than about 10 cm, less than about 5 cm, less than about 3 cm, or less than about 2 cm, or less than 1 cm. In some embodiments, when a cassette electrophoresis base is placed on top of a light source with a flat upper surface, the distance from the upper surface of the light source to the lower wall of the cassette is from 0 to 2 mm, from 2 to 4 mm, from 4 to 6 mm, from 6 to 8 mm, or from 8 to 10 mm.

The power supply base in preferred embodiments has programmable settings, such as for electrophoresis time, current, and/or voltage, and in preferred embodiments the polarity of the electrical current can be reversed by means of a switch or button.

The electrophoresis cassette base preferably incorporates an AC/DC adapter, such that in can be plugged into a standard electrical outlet and the base includes, or can be connected to, a connector, or power cord, that can be plugged into a standard electrical outlet (output from 100-240 VAC, 50/60 Hz). The power output of the power supply base can be in the range of about 5 to about 240 VDC, for example, from 10-240 VDC, or from 20-100 VDC, or about 48 VDC, and in exemplary embodiments has a minimum current output of about 0.4 A, 0.5 A, 0.6 A, 0.7 A, 0.8 A, 0.9 A, or 1 A. The power supply in some exemplary embodiments can change the anode and cathode polarity. In these embodiments, a switch in anode and cathode polarity can be controlled by the user by means of a switch, dial, or button.

The power supply base can be programmed with one or, preferably, more than one, electrophoresis programs. The program(s) can determine the voltage or current supplied during electrophoresis and/or the duration of electrophoresis. In some exemplary embodiments, at least one program is a "reverse" program that allows the user to switch the anode and cathode polarity. The programs in certain embodiments are modifiable by the user, such as by use of buttons provided on a panel of the power supply electrophoresis cassette base. The power supply base preferably also an on/off switch or button, and an LCD display that displays at least one of: the program being run, the time remaining in the electrophoresis run, the voltage, or the current. The power supply electrophoresis cassette base can further include an indicator light, that can, for example, be an LED light, to indicate when the power supply is on, and an alarm that emits a sound to indicate that the electrophoresis run has been completed.

The power supply electrophoresis cassette base preferably includes a program or control switch or button that allows the user to switch the polarity of electrophoresis. In some preferred embodiments, a "reverse" program is included that the user is able to select using control buttons. The reverse program can reverse the polarity for a given period of time, for example, from 15 seconds to 15 minutes, or from 30 seconds to 10 minutes, or from one minute to five minutes. The voltage output during the reverse program can be the same or different from the voltage output used during a standard electrophoretic separation program.

In some exemplary embodiments, the cassette is used for protein, peptide, or nucleic acid molecule or nucleic acid fragment isolation, for example using a cloning cassette that comprises a gel having two or more wells, in which at least at least a first well and a second well of the two or more wells are aligned in a single electrophoresis lane, and the cassette has apertures over the wells for loading a sample in a first well, and extracting a separated fragment from a second well. Such a cloning cassette is described in U.S. Provisional Patent Application 60/824,210, filed Aug. 31, 2006 and U.S. Provisional Patent Application 60/829,517, filed Oct. 13, 2006, both of which are incorporated herein by reference in their entireties.

In some exemplary embodiments, when a cassette is positioned on the base, a light source can be inserted into the space in the base that is below the cassette, or the cassette electrophoresis base can be positioned on a light source base that includes a light source, in which the portion or surface of the light source base from which light is emitted is directly below a cassette positioned on the electrophoresis base for electrophoresis. In these embodiments, the space beneath the cassette (from the bottommost surface of the cassette electrophoresis base where it contact the surface it rests on, to the bottom wall of the cassette) is at least 2 mm and can be, for example, from 2 to 4 mm, from 4 to 6 mm, from 6 to 8 mm, or from 8 to 10 mm, from 1 cm to 2 cm, from 2 cm to 4 cm, from 4 cm to 6 cm, from 6 cm to 8 cm, from 8 cm to 10 cm, or greater than 10 cm. The light source base can be of any type that directs light upward (toward a cassette positioned on the base). The light emitted by the light source can be of any wavelength range, for example in the UV, visible, or infrared wavelengths, or a combination thereof. Molecular separation can therefore be viewed as it is occurring during electrophoresis by means of a light source that is part of a light source base positioned underneath the cassette electrophoresis base.

In embodiments in which the cassette electrophoresis base is positioned over a light source base, the light emitting surface of the light source base occupies at least a portion of the space beneath the cassette in the electrophoresis base, and in some embodiments occupies such as 90% or more, 95% or more, or 97% or more, or essentially all of the open space beneath a cassette positioned in the electrophoresis base. In exemplary embodiments, the cassette electrophoresis base is positioned over a light source base that includes a light source that fits the space in the electrophoresis base that is directly below a cassette positioned in the electrophoresis base.

The invention therefore includes in illustrative embodiments an electrophoresis system that includes cassette electrophoresis base that supports a cassette during electrophoresis and comprises a power supply and a light source base that can reversibly engage the cassette electrophoresis base such that light is directed upward into a cassette supported by the cassette electrophoresis base. In preferred embodiments, the light source base is configured such that the size of the light emitting portion of the light source base conforms to the size of the opening, or space, in the cassette electrophoresis base to direct light upward into the cassette and the light source base does not emit light outside the boundaries of the cassette.

The cassette electrophoresis base can simply be positioned over the light source base, or can reversibly engage a light source base by any feasible means. For example, in some exemplary embodiments the light source base can comprise regions having slots or grooves that can be slidably engaged by the electrophoresis cassette base, or can have one or more guides, tabs, rims, shoulders, pins, bumps, posts, flanges, or snaps, or the base can have one or more guides, tabs, rims, shoulders, slots, grooves, pins, bumps, posts, flanges, or snaps, for guiding the positioning of the base on the light source base and/or engaging the light source base. In some exemplary embodiments, one or more tabs, rims, shoulders, bumps, posts, pins, or other protrusions on one or more lower surfaces of the cassette electrophoresis base fit into one or more holes, slots, depressions, or guides on one or more upper surfaces of the light source base to position the cassette electrophoresis base on the light source base. In some exemplary embodiments, one or more tabs, rims, shoulders, bumps, posts, pins, or other protrusions on one or more upper surfaces of the light source base fit into one or more holes, slots, depressions, or guides on one or more lower surfaces of the cassette electrophoresis base to position the cassette electrophoresis base on the light source base.

The light source base can include a electrical connector (power cord) separate from that of the cassette electrophoresis base and an on/off switch or button separate from that of the cassette electrophoresis base.

The light source base can optionally include a filter that filters light emitted by the light source as described herein, referred to as an excitation filter. An excitation filter can comprise glass, plastics, gels, acrylics, etc., and can have any wavelength cutoff. In some preferred embodiments, an excitation filter used in the devices and methods of the invention has a wavelength cutoff of between about 480 nm and about 485 nm, between about 485 nm and about 490 nm, between about 490 nm and about 495 nm, between about 500 nm and about 505 nm, between about 505 nm and about 510 nm, or between about between about 510 nm and about 515 nm, in which light of wavelengths above the cutoff value is not transmitted through the filter. For example, an excitation filter in certain embodiments in which the light source is a blue light source can have a light wavelength cutoff of about 480 nm, about 485 nm, about 490 nm, about 495 nm, about 500 nm, about 505 nm, about 510 nm, or about 515 nm, in which light above the specified wavelength is not transmitted through the filter. Examples of blue filters (for transmitting blue excitation light) that can be used as excitation filters incorporated into a light source base, incorporated into the wall of a cassette, or provided as a separate piece to be interposed between a light source and a sample include but are not limited to, a Perspex blue filter 750 (made by Lucite), an Acrylite #668-0GP filter (made by Cyro), a Lighting gels sky blue 068 filter (made by Format) and a Kopp Blue 5543 filter (made by Kopp). The thickness of the filter can vary, for example, from about 0.2 mm to about 6 mm, or from about 0.4 mm to about 4 mm, as can the distance from the filter to the light source, which can range, for example, from about 2.5 m, to about 50 mm, for example from about 5 mm to about 30 mm.

In some embodiments, the bottom wall of a cassette used in a cassette electrophoresis base can filter light emitted by the light source. In other embodiments, one or more filters for filtering light emitted by a light source used in a light source base of the invention can be separated from the light source base and a cassette used for electrophoresis. For example, a separate filter used in conjunction with a light source base can be placed over the light emitting surface of the light source base to filter out light that is not absorbed by a fluorophore to be used in electrophoresis, for example, a fluorophore used to stain or label a biomolecule to be separated. In some embodiments, the light source has an emission spectrum that can be used to excite fluorphores that absorb at different wavelengths. In some embodiments, a light source base that emits, for example, visible light over a wavelength range that can excite fluorophores that maximally absorb at different wavelengths, can be used with more than one excitation filter (where the filters can be reversibly positioned over the light emitting portion of the light source base, or alternatively, can be fitted to the bottom of a cassette) in which one filter can be selected to transmit light that can activate a first fluorophore, and a second filter can be selected to transmit light that can activate a second fluorophore. One, two, three, four, or more excitation filters can thus be used separately to optimize visualization of different fluorphores that may be present in the same or different electrophoretic separations.

A filter that filters light emitted by fluorophores in the sample (e.g., gel, cassette, dish, slide, well, membrane, or filter) as described herein, referred to as an emission filter, can be provided with a light source base as a piece that can fit over a sample (between the sample and the viewer or imaging system), or can be incorporated into the wall of a cassette, or provided in the form of goggles, for example. An emission filter can comprise glass, plastics, gels, acrylics, etc., and can have any wavelength cutoff. In some exemplary embodiments, an emission filter used in the devices and methods of the invention can have a wavelength cutoff of between about 485 nm and about 490 nm, between about 490 nm and about 495 nm, between about 500 nm and about 505 nm, between about 505 nm and about 510 nm, of between about between about 510 nm and about 515 nm, of between about 515 and 520 nm, or of between about 520 nm and about 525 nm, where light of a wavelength below the cutoff value is not transmitted through the filter. For example, an emission filter in certain embodiments in which the light source is a blue light source for exciting fluorophores can have a light wavelength cutoff of 485 nm, 490 nm, 495 nm, 500 nm, 505 nm, 510 nm, 515 nm, 520 nm, or 525 nm in which light below the specified wavelength is not transmitted through the filter. Examples of amber filters that can be used as emission filters that can be used in viewing goggles, incorporated into the upper wall of a cassette, or provided as a separate piece to be interposed between a sample and a viewer or an imaging system include but are not limited to, a Perspex amber filter 300 (made by Lucite), an Acrylite #303-0GP filter (made by Cyro), a Lighting gels medium amber 020 filter (made by Format), a Knight Optical Yellow filter (made by Knight) and a Kopp Sharp cut red 3482 filter (made by Kopp). The thickness of the filter can vary, for example, from about 0.2 mm to about 6 mm, or from about 0.4 mm to about 4 mm.

Preferably, a cassette comprises at least one dye that binds biomolecules (e.g., proteins, peptides, or nucleic acid molecules), or samples include at least one dye when they are loaded in the gel. Preferably a dye used to label biomolecules is a fluorescent dye that absorbs light of a wavelength that is transmitted through the bottom wall of the cassette and emits light of a wavelength that can transmit through the upper wall of the cassette. (The upper wall of the cassette can optionally include a filter to filter out light of wavelengths that are not emitted by the excited fluorophore dye. In an alternative, a viewer can place a filter over the cassette, or can use filtered glasses or a camera or imager that includes a filter for viewing or imaging the gel.) Examples of dyes, light sources, and filters that can be used for visual detection of electrophoresing biomolecules such as nucleic acids and proteins are described herein.

In some embodiments, two or more dyes may be present in the same electrophoresis cassette. Different dyes may be used to stain different types of biomolecules, for example, a first fluorophore may be used to label a first biomolecule or class of biomolecules, and a second fluorophore may be used to label a second biomolecule or class of biomolecules, where the first and the second fluorophores have different emission spectra, and where the first and second biomolecules can be in the same or different samples electrophoreses using the devices and methods of the invention. In this case, different emission filters can be used for optimal visualization of biomolecules in the cassette stained with the different fluorophores.

The invention thus provides in exemplary embodiments an electrophoresis system for viewing and running an electrophoresis gel that comprises a base for positioning the cassette during electrophoresis (an "cassette electrophoresis base") that comprises at least two electrical contact points for contacting electrodes of a cassette positioned on the base and at least one connector that can connect to a power source, such as an electrical outlet; and further includes a light source base configured to reversibly engage the cassette electrophoresis base. The cassette electrophoresis base is therefore a power supply on which a cassette can be positioned during electrophoresis, in which the power supply can supply a set current through the cassette and/or provide a set voltage across the electrodes of a cassette positioned on the base. The cassette electrophoresis base is configured to engage a cassette along at least one edge of the cassette. The cassette electrophoresis base is configured such that when a cassette is positioned in the base, there is a space underneath the cassette in the region of the cassette in which electrophoretic separation occurs. (That is, underneath the region of the cassette corresponding to the region of the gel in which molecular separation occurs, the base does not have any structures, but rather is open, such that there are no parts of the base that block or obscure transmission of light upward into the cassette from a light source positioned underneath the cassette).

The light source base includes a light source that, when positioned under the electrophoresis base, directs light upward into a cassette positioned in the electrophoresis base. The light source base includes a power cord and preferably also includes an on/off switch.

The electrophoresis cassette base of the electrophoresis running/viewing system also has an on/off switch and preferably one or more additional switches, buttons, or dials that control one or more of the voltage or current output, the programmed duration of voltage or current output, the elapsed time of voltage or current output and/or the polarity of the current. The base/power supply preferably also has a display panel, such as a liquid crystal display (LCD) panel or an LED display panel that communicates at least one of elapsed time of an electrophoresis run and the voltage or current output.

The invention includes methods of separating biomolecules using a cassette electrophoresis base that includes a power supply that is positioned over a light source base. In performing these methods, a cassette that contains a gel is positioned on a cassette electrophoresis base of the invention that is positioned over a light source base. The gel has one or more wells for the loading of sample and the cassette comprises one or more openings in at least one wall of the cassette that access the wells. One or more samples having one or more biomolecules to be separated are loaded in at least one of the one or more wells of the gel. The cassette (for example, the gel, ion source, buffer, or other repository within the cassette), the sample, or both include at least one fluorophore that is bound to or can bind to at least one biomolecule in the sample to provide at least one stained biomolecule. One or more biomolecules in one or more samples loaded on the gel are electrophoretically separated by turning on the power supply of the cassette electrophoresis base to provide current for electrophoretic separation of stained biomolecules within the cassette. The one or more stained biomolecules in the cassette can be visualized during and after electrophoretic separation using the light source of the light source base. Optionally, the gel can also be imaged using an overhead camera or imaging system positioned over the electrophoresis base holding the cassette.

The invention in other aspects provides a base for viewing and running an electrophoresis gel that comprises a base for positioning the cassette during electrophoresis (an "integrated electrophoresis cassette base") that comprises at least two electrical contact points for contacting electrodes of a cassette positioned on the base and at least one connector that can connect to a power source, and also comprises at least one light source that can emit light into a cassette positioned on the base. The integrated electrophoresis cassette base is therefore a combined power supply/light source on which a cassette can be positioned during electrophoresis, in which the power supply can supply a set current through the cassette and/or provide a set voltage across the electrodes of a cassette positioned on the base. The electrophoresis cassette base has an on/off switch and preferably one or more additional switches, buttons, or dials that control one or more of the voltage or current output, the programmed duration of voltage or current output, and/or the elapsed time of voltage or current output. In some preferred embodiments, the cassette electrophoresis base with integrated light source has one or more controls that reverse the polarity of the anode and cathode, such that electrophoresis can occur in one direction (typically proceeding from the wells toward the anode), and subsequently the direction of electrophoresis can be reversed. The base/power supply preferably also has a display panel, such as a liquid crystal display (LCD) panel or an LED display panel that communicates at least one of elapsed time of an electrophoresis run and the voltage or current output.

The electrophoresis cassette base in these aspects also includes an integral light source, such as a UV light or visible light source as described herein, that is positioned such that light can be transmitted to a gel in a cassette positioned on the base. Preferably, light is transmitted from a light source below a cassette positioned horizontally on the base, such that light is transmitted upward through the bottom wall of the cassette. As disclosed above, a light source need not be positioned directly below the gel cassette, but can be angled away from the cassette and the emitted light can be directed to the cassette or a portion thereof using one or more mirrors. The light source is preferably a visible light source, and can comprise one or more LEDs, as disclosed above. In some illustrative embodiments, an integrated cassette electrophoresis viewing and running base comprises a light source that includes from two to 500 LEDs that emit blue light. Preferably in an electrophoresis system conforming to this electrophoresis base embodiment a blue light filter (transmitting blue light) is positioned between the light source and a cassette positioned on the base, and a second filter that allows transmission of light emitted from a fluorophore in the cassette is positioned between the cassette and a viewer or detection device.

Preferably a dye used to label biomolecules separated in the cassette is a fluorescent dye that absorbs light of a wavelength that is transmitted through the bottom wall of the cassette and emits light of a wavelength that can transmit through the upper wall of the cassette. (The upper wall of the cassette can optionally include a filter to filter out light of wavelengths that are not emitted by the excited fluorophore dye. In an alternative, a viewer can place a filter over the cassette, or can use filtered glasses or a camera or imager that includes a filter for viewing or imaging the gel.) Examples of dyes, light sources, and filters that can be used for visual detection of electrophoresing biomolecules such as nucleic acids and proteins are described herein.

In some embodiments, two or more dyes may be present in the same electrophoresis cassette. Different dyes may be used to stain different types of biomolecules, for example, a first fluorophore may be used to label a first biomolecule or class of biomolecules, and a second fluorophore may be used to label a second biomolecule or class of biomolecules, where the first and the second fluorophores have different emission spectra, and where the first and second biomolecules can be in the same or different samples electrophoreses using the devices and methods of the invention. In this case, different filters can be used for optimal visualization of biomolecules in the cassette stained with the different fluorophores.

In some exemplary embodiments, the method includes imaging the gel during or after electrophoresis using an imaging system that fits over the cassette electrophoresis base. In some exemplary embodiments, the method includes imaging the gel during or after electrophoresis using an imaging system that is positioned underneath the cassette electrophoresis base.

In another aspect, the invention provides an imaging system for gels that includes a light source and detector that are integrated into a base unit that can support one or more gel cassettes during electrophoresis. In these embodiments, the base unit of the electrophoresis imaging system preferably provides contact points for connecting electrodes of the cassettes to a power source. In some preferred embodiments, the light source and detector unit of the base are positioned below the one or more cassettes that are positioned on the base, one or more optical filters is positioned between the light source and the cassette(s), and one or more additional filters is positioned between the cassettes and the detector, and light emitted from fluorophores in the gel cassette is directed to the detector by one or more mirrors. Either or both of the light source and a detector need not be directly (orthogonally) below the cassette, but can be below the level of the cassette and offset or angled, where either or both of the light emitted by the light source and the light detected by the detector are direct toward and away from the cassette by one or more mirrors. The pattern of fluorescence can also, in preferred embodiments, be viewed from above during and after electrophoresis, using light provided by the light source and, preferably, an emission filter to enhance visibility of the fluorophores. Thus, viewing and imaging can occur simultaneously on a gel during electrophoresis.

In one embodiment, the light source comprises one or more light emitting diodes, as disclosed above. In some embodiments, one or more fluorophores are provided in a gel cassette. In preferred embodiments of the method, a fluorophore provided in the cassette or in the sample absorbs in the visible light range. In these embodiments, fluorescence of stained biomolecules in the cassette can be viewed by a user from above looking down on the cassette, and can be detected by a detection device positioned below the cassette.

The invention includes methods of using a gel cassette electrophoresis base to separate one or more biomolecules, in which the method includes: positioning a cassette that comprises electrodes, at least one gel, and at least one ion source on a cassette electrophoresis base of the invention that includes a light source for illuminating the cassette, loading one or more samples comprising at least one biomolecule into the gel, turning on the power to provide current through the cassette for electrophoretic separation, thereby separating one or more biomolecules using an electrophoresis base of the invention. In preferred embodiments, the method includes viewing the gel after electrophoresis while the gel remains in the cassette and the cassette remains positioned on the base. In preferred embodiments, the gel, the sample, or both contain at least one dye. In preferred embodiments, the method includes viewing the gel during electrophoresis while the gel remains in the cassette and the cassette remains positioned on the base.

The invention also includes methods of using a gel cassette electrophoresis base to separate one or more biomolecules, in which the method includes: positioning a cassette that comprises electrodes, at least one gel, and at least one ion source on a cassette electrophoresis base of the invention that includes a light source for illuminating the cassette and a detector for detecting fluorescence, loading one or more samples comprising at least one biomolecule into the gel, turning on the power to provide current through the cassette for electrophoretic separation, thereby separating one or more biomolecules using an electrophoresis base of the invention. In preferred embodiments, the method includes imaging the gel during or after electrophoresis while the gel remains in the cassette and the cassette remains positioned on the base. In preferred embodiments, the gel, the sample, or both contain at least one dye. In preferred embodiments, the method includes imaging the gel during electrophoresis while the gel remains in the cassette and the cassette remains positioned on the base. In preferred embodiments, the method includes imaging and viewing the gel during electrophoresis while the gel remains in the cassette and the cassette remains positioned on the base.

In yet another aspect, the invention provides an illumination system or "scanner" for imaging electrophoresis gels, in which the light source for illuminating stained biomolecules within the gel and the detection unit are both positioned underneath the gel or gel cassette. In these embodiments, a light source, which is preferably a visible light source, projects light upward from below the lower surface of a gel (which may or may not be within a cassette). The light passes through a filter that filters out at least a portion of the light that does not excite a fluorophore present in the gel that is used to stain at least one biomolecule or at least one class of biomolecules. Light produced by the fluorophore(s) in the gel that is directed downward also passes through a filter before encountering a detector used to image the gel. Light from the light source used to illuminate the gel can optionally be directed toward the gel by means of one or more mirrors. Light produced by fluorophores within the gel can also be by means of one or more mirrors to the detector. In this way, through positioning of the light source, mirrors, detector, the "flatbed scanner" can be designed such that the light paths do not interfere with one another.

Figure 9:
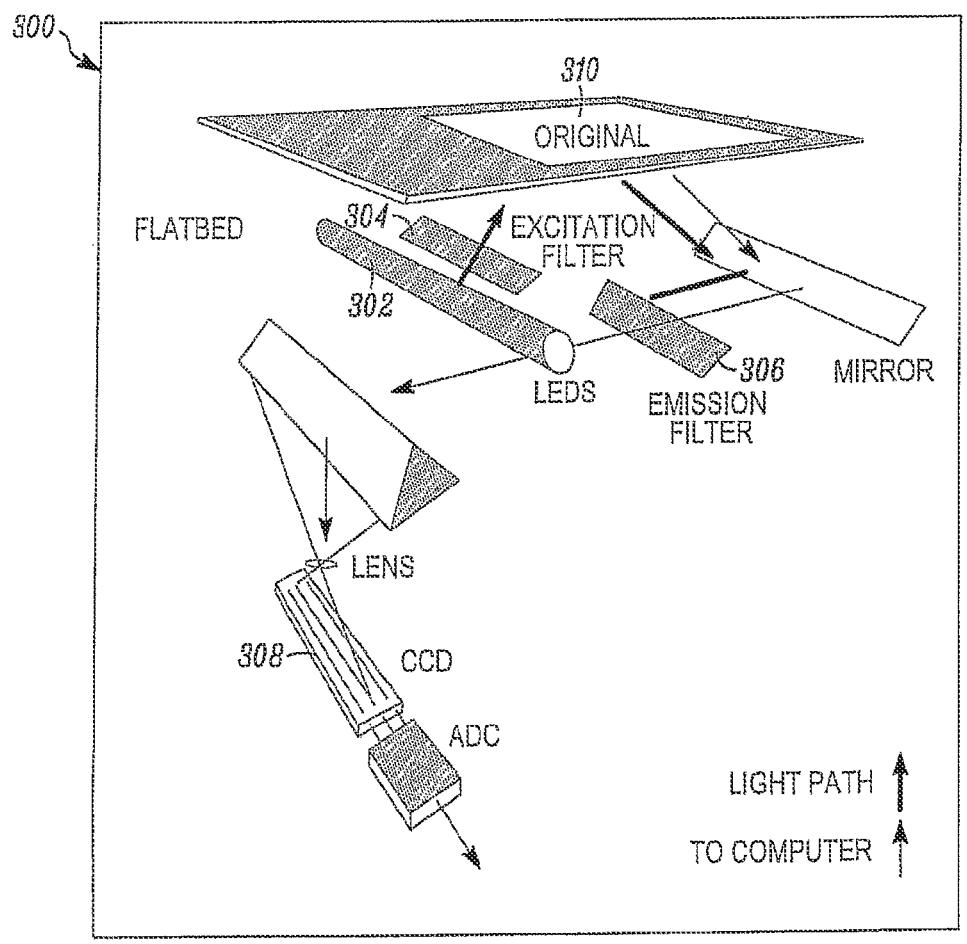
FIG. 9 is a schematic illustration of a system for electrophoresis imaging, constructed and operative in accordance with another embodiment of the present invention.

One design of this type of scanner is depicted in FIG. 9. In this design the light source (here, LEDs) (302) is positioned below the level of the gel cassette, but not directly (orthogonally) below the gel or gel cassette, such that light produced by light source comes at the gel cassette from an angle. The light from the light source passes through a filter that filters out at least a portion of the light that is of a wavelength that is not absorbed by a fluorophore present in the gel cassette. Light emitted by one or more fluorophores in the gel is directed to a detector as shown by a mirror. A flatbed scanner using a visible light source as described herein can also be used for membranes (e.g., blots), plates, dishes, or arrays, for detection of labeled biomolecules, in which one or more biomolecules present on a membrane, plate, or array, or in a well or dish is labeled with a fluorophore.

Certain embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Figure 2:
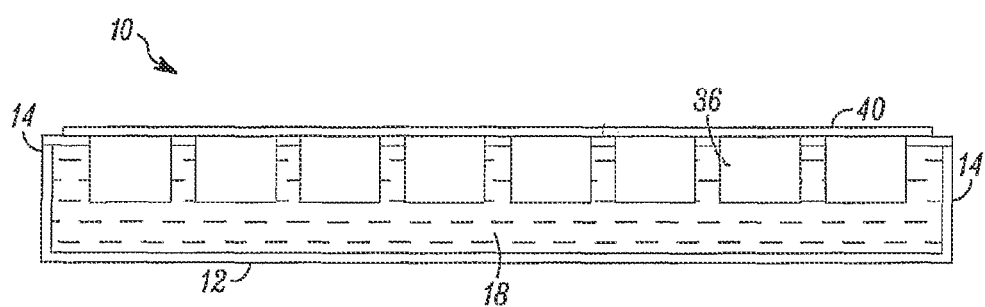
FIG. 2 is a schematic cross section illustration along lines II-II in FIG. 1.
Figure 3:
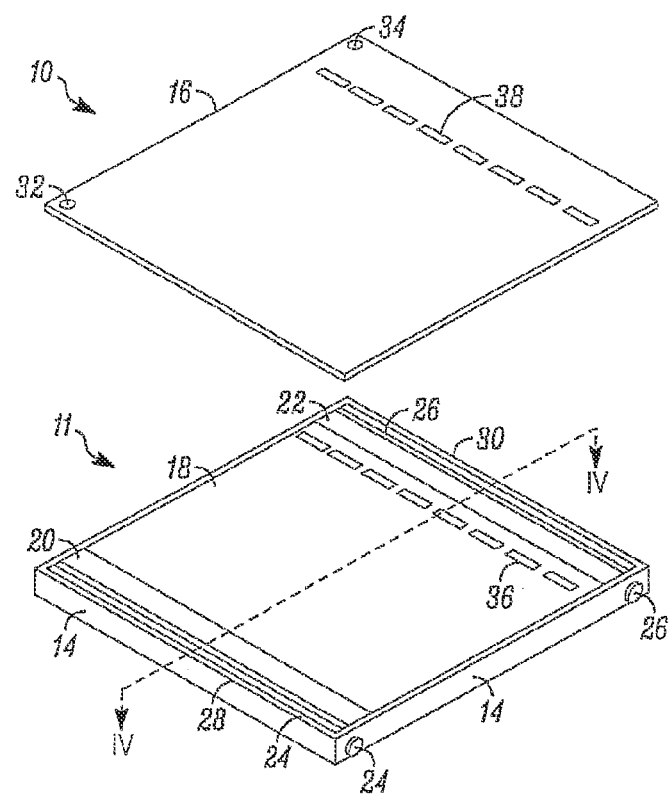
FIG. 3 is a schematic isometric exploded illustration of the electrophoresis cassette of FIG. 1.

Referring now to FIGS. 1-3, an electrophoresis disposable cassette 10 is illustrated. Cassette 10 is constructed and operative in accordance with one embodiment of the present invention. Alternative cassette configurations and designs that may be used in the present invention include but are not limited to those disclosed in U.S. Pat. No. 5,582,702, U.S. Pat. No. 5,865,974, and U.S. Pat. No. 6,379,516, the entire contents of which are incorporated herein by reference.

Cassette 10, as best seen in FIG. 1, is a closed disposable cassette preferably, but not necessarily, used for a single electrophoresis test. Cassette 10 includes all the chemical compounds required for driving the electrophoretic separation of biomolecules such as DNA, RNA, or proteins.

As best seen in FIG. 3, the cassette 10 preferably comprises a three dimensional chamber 11 which may be generally flat, having a bottom wall 12 (seen in FIG. 2), side walls 14, and a top wall or cover 16, in which the chamber of the cassette houses a gel 18 and can include within it one or more fluorophores. In one embodiment, the bottom wall 12 may be made of any suitable material that is transparent to light of a wavelength emitted by the light source, such as the TPX plastic commercially available from MITSUI of Japan or the PMMA plastic, commercially available from Repsol Polivar S.P.A. of Rome. The top wall 16 may be made from a similar material, however, top wall 16 is in this embodiment configured with a filtering property to filter the light emitted from the light source that is not of a wavelength emitted by a dye used to stain biomolecules in the sample that may be provided in the cassette. In this regard, the emission filter built into the cassette cover would allow only the emission light of a fluorophore to pass, blocking the majority of the excitation light (e.g., in some preferred embodiments not allowing any light below around 520 nm to be transmitted but allowing most light above 520 nm to be transmitted).

In one embodiment of a method for producing cassette 10, a plastic molding process is employed utilizing a Rohaglas Molding Powder, commercially available from Sidas GmbH of Damstadt, Germany. One skilled in the art will appreciate, a number of design considerations must be addressed when selecting a suitable material for the top wall of the cassette 16, including:

1) material spectral properties (i.e. does it let the light emitted by the fluorophore transmit at a high enough level, but still block the unwanted excitation light);

2) material autofluorescent properties (i.e. does the emission filter "glow" in the absence of fluorophores when excitation light hits it);

3) material ability to be cast or molded into the proper cassette form; and 4) material chemical compatibility with electrophoresis (i.e. does it bind the nucleic acid stain, or degrade when in contact with the electrophoresis buffers).

Figure 4:
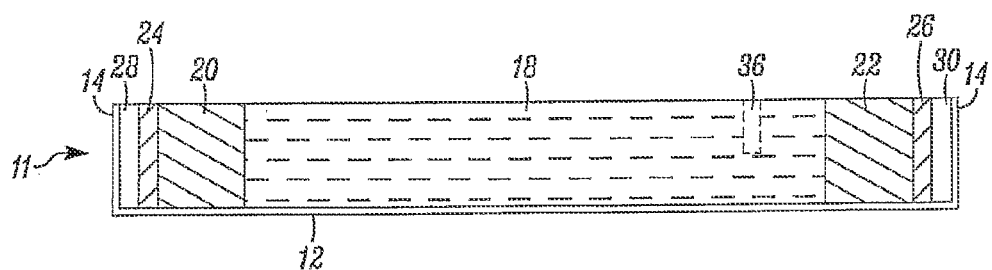
FIG. 4 is a schematic cross section illustration along lines IV-IV in FIG. 3.

In one embodiment, top wall 16 may be made from an acrylic material. One suitable acrylic material is ARG/KTP material commercially available from NOIR laser (www.noirlaser.com). The ARG/KTP material may be modified with a mixture of additives such that a shift of wavelengths can be realized to reduce autofluorescence as needed. Furthermore, the ARG/KTP acrylic material from NOIR laser may be cast into the shape of As best seen in the cross section illustration of FIG. 4, chamber 11 houses a gel 18 which may be any suitable gel for electrophoresis, such as an aqueous gel or a gel made of agarose, acrylamide, or composites thereof. In one embodiment, gel 18 comprises a nucleic acid stain, such as, for example, a SYBR® dye. In another embodiment, a cation exchange matrix 20 and an anion exchange matrix 22, collectively referred to as the ion exchange matrices 20 and 22, may also be housed within chamber 11. One or more ion exchange matrices present in a cassette can be a source of ions for electrophoresis. In some embodiments, an ion exchange matrix is provided at one end of the cassette, such as an anion exchange matrix at the cathode end. Chamber 11 further comprises two electrodes configured as conductive rods referenced 24 and 26, such as, for example, copper, lead, carbon, or aluminum, rods which, when connected to an external direct current (DC) electrical power source, provide the electric field required to drive electrophoretic separation. In the illustrated embodiment, rod 24 is the anode and rod 26 is the cathode. Chamber 11 further can optionally comprise one or, as shown, two empty volumes 28 and 30, that gases produced during the electrophoresis test can occupy. Alternatively or in addition, the open cover 16 may include two vent holes 32 and 34, shown only in FIG. 3, for venting the gases generated during electrophoresis.

Cassette 10 preferably also includes wells 36 in the gel 18. Wells 36 are used to introduce samples of the molecules which are to undergo electrophoretic separation. The wells 36 may be formed by any suitable method, such as by introducing a comb (like structure 40 in FIG. 2) to the gel during the assembly of the gel. The comb 40 is introduced to the gel via corresponding openings 38 (FIG. 3) in the top wall of the cassette 16. The openings 38 may be used as an additional space for loading the molecular samples just before the onset of the electrophoresis test after the comb 40 is removed.

According to a preferred embodiment of the present invention, as best seen from FIG. 2, the wells 36 are covered by the comb 40 used in their preparation. This is since the comb method involves insertion of a comb structure into the gel via the openings 38 in the top wall 16, the comb being pulled out only just before the electrophoresis test. In this regard, cassette 10 is generally a closed cassette covered by the comb 40 which is removed just before the electrophoresis test itself.

In one embodiment, the cassette 10 may also include a dye source. For example, in FIG. 4, a cation exchange matrix 20 can release not only the cations for electrophoresis (for example, Tris cations) but also one or more dyes which interact with the molecules undergoing electrophoretic separation. In some embodiments, the system can have a UV light source incorporated into the base, and ethidium is provided in the cation exchange matrix, such that ethidium ions are released during electrophoresis to stain nucleic acid molecules.

In another embodiment, an anion exchange matrix 22 can provide a dye source to stain the protein or nucleic acid molecules so as to enable their visualization and analysis, in situ, utilizing a suitable electrophoresis system, such as the system described with reference to FIG. 5 hereinbelow.

Figure 5:
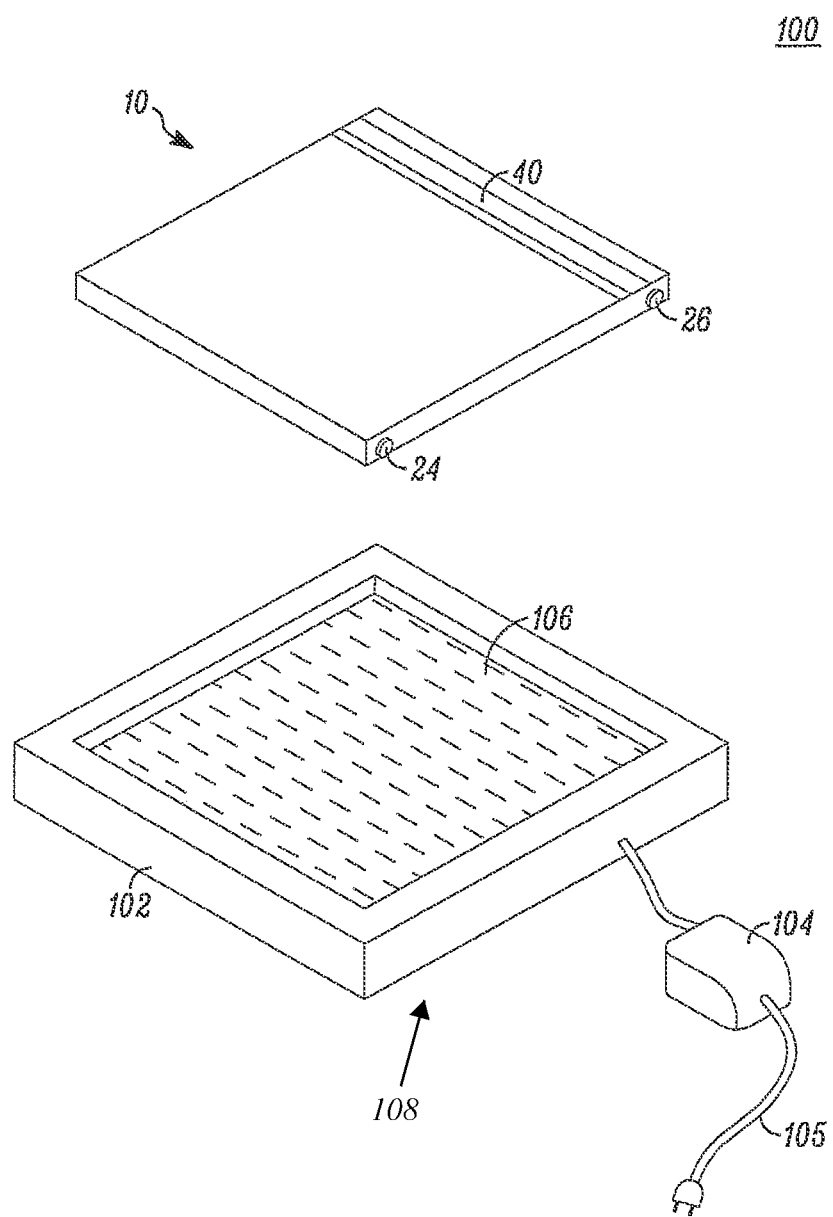
FIG. 5 is schematic isometric illustration of a system for electrophoresis, constructed and operative in accordance with another embodiment of the present invention.

Referring now to FIG. 5, a schematic isometric illustration of a system for conducting a plurality of electrophoresis tests is shown. The system is suitable for visualizing and documenting, in situ, the results of the electrophoresis tests, and is constructed and operative in accordance with one embodiment of the present invention. The system, generally referenced 100, generally comprises a base 102 for supporting a cassette 10 or other similar cassettes that also serves as a power supply for providing the direct current (DC) required for driving the electrophoresis separation process, an AC/DC adaptor 104 for converting an AC power source (such as from an electrical outlet) to DC, a power cord 105 for connecting the cassette base to an electrical outlet and a visible light source 106, such as LEDs emitting in the blue wavelength integrated into the base 102 for illuminating the cassette 10. The cassette is substantially enclosed, having an inserted comb 40 that is removed prior to loading of samples in the wells.

Cassette base 102 designed to fit the dimensions of the cassette 10, and comprises two contact points (not shown) to which the electrode rods 24 and 26 of the cassette 10 are connected so as to provide thereto the electric field required for the electrophoresis separation. Alternate configurations include those in which one or more edges or the cassette slide into grooves in the cassette base, or, for example, the cassette can snap into position on a base at one or more edges of the cassette.

In another embodiment, system 100 may also comprise means for documenting the electrophoresis separation results. In the illustrated embodiment these include a camera, which can be a video camera and the documentation system can include a computer operatively connected to camera and executing any suitable application for image analysis of the results of the electrophoresis separation.

It is a particular feature of system 100 that both the electrophoresis test, the visualization of the results thereof and optionally the documentation and the analysis thereof are performed when the cassette is in situ, i.e. in holder 102.

Unlike prior art electrophoresis systems for DNA molecules separation where the gel is taken and immersed in a UV sensitive marker, typically ethidium bromide, after the test, in one embodiment of cassette 10 a dye that is detectable using visible excitation wavelengths is included in the cassette (such as in the body of gel) as described hereinabove so as to enable the visualization and thus the documentation and analysis of the electrophoresis test results. In another embodiment, a nucleic acid stain, such as a SYBR® dye is included in the cassette so as to enable visualization as described above.

In the embodiment illustrated in FIG. 5, the holder 102 is a stand alone open box-like construction which includes a light source 106 and a support surface above the light source on which a cassette 10 is placed. In one alternative, it may include a bottom support surface 108 that includes a filter for the selective transmission of particular wavelengths of light.

Figure 6:
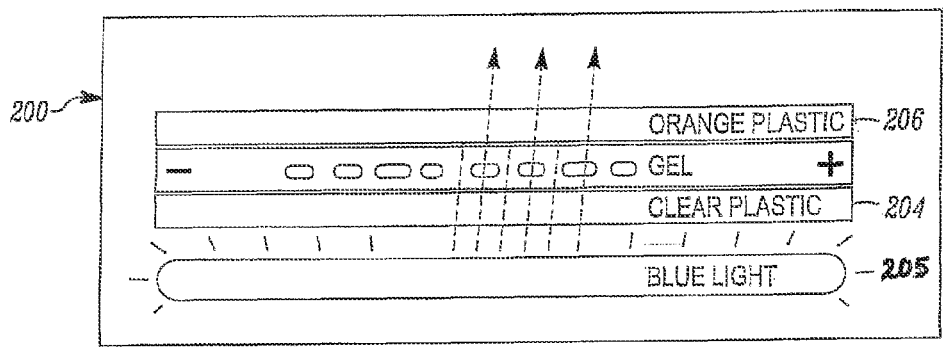
FIG. 6 is a cross-sectional view of one embodiment of an illumination system having a light source that emits blue light upward through a cassette having a clear plastic lower wall and an orange plastic upper wall.
Figure 7:
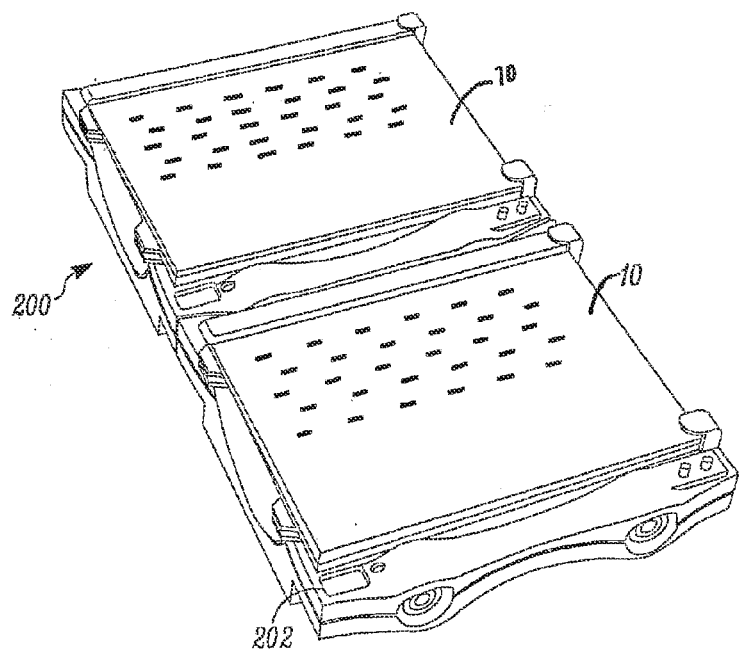
FIG. 7 depicts a cassette electrophoresis base having two cassettes positioned on the base, a light source positioned below the cassettes excites fluorophore within the gel cassettes to provide an image of separated molecules stained with the fluorophore.
Figure 8:
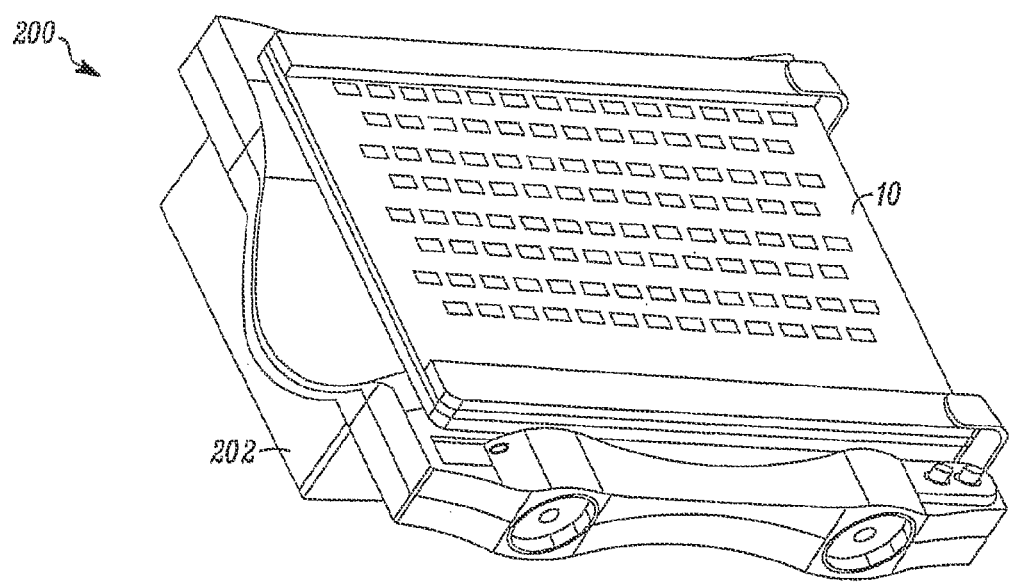
FIG. 8 depicts a cassette electrophoresis base having an integral light source positioned below a cassette positioned on the base.

Referring to FIGS. 6-8, in another embodiment, system 200 may be an extension of the E-BASE™ power system and E-GEL® cassette gels, products commercially available from Invitrogen (Carlsbad, Calif.). In this regard, cassette holder 102 may comprise an E-BASE™ power system unit 202 that is modified with an ability to emit blue light from below for excitation of the fluorophore containing electrophoretic gel. When used in combination with cassette 10, described above, the emission light would pass through the lower wall 204 of the precast gel cassette 10. In one embodiment, when SYBR® dyes are used, then the excitation light may have an emission around 480 nm and have little to no emission above about 520 nm or so (either by design or by the inclusion of an excitation filter that could be provide as part of the power system unit 202 or part of the lower wall of the cassette 204). The end result would be that a user may look at the gel and see only the areas where the nucleic acid stain had bound to nucleic acid and become fluorescent, while all other areas would appear black, as best seen, for example, in FIG. 7. Colored light from light source 205, (in this case "blue"/470 nm to optimally excite SYBR® dyes) passes through the bottom wall 204 of a precast gel cassette, such as cassette 10, excites any fluorescent stains or dyes, and the emission light passes through an emission filter 206 (which blocks all of the original excitation light) that is integrated into cassette 10. The emission light can either be directly viewed by the user to monitor the progress of an electrophoresis run or can be photographed, recorded, or otherwise imaged to document the results.

One advantageous feature of the present invention is that it may eliminate some of the inconvenience of imaging electrophoretic gels. When the user snaps a gel cassette, such as cassette 10, into the base 202 it can be visualized immediately and with no further steps. The excitation light, excitation filter, gel, power base and nucleic acid stain are all integrated in a single electrophoresis system. A user may simply press a button and watch the gel run. The user avoids having the gel run too far as the gel run can be monitored in real time. The device is configured such that a user may be able to see the gel run in normal to dim room lighting without having to move the unit into a darkroom.

Referring again to FIGS. 5-8, one skilled in the art will appreciate that one particular feature of the systems 100, 200 is that relative to prior art, a smaller number of operations is required from the user in order to conduct an electrophoresis test employing cassette 10. These steps, for electrophoresis separation of DNA molecules, include:

A. A sample which includes the protein or nucleic acid molecules to be separated is introduced in wells;

B. The electrical current is switched on;

C. As a result of steps A and B; both electrophoresis separation and interaction of a visible light detectable dye with the separated biomolecules take place at the same time such that the interaction is viewable throughout the process;

D. The viewer observes the separation at one or more timepoints during the electrophoresis, and optionally, records the image, such as by use of a camera;

E. The user turns the base power supply off and disposes of the cassette 10.

Figure 10:
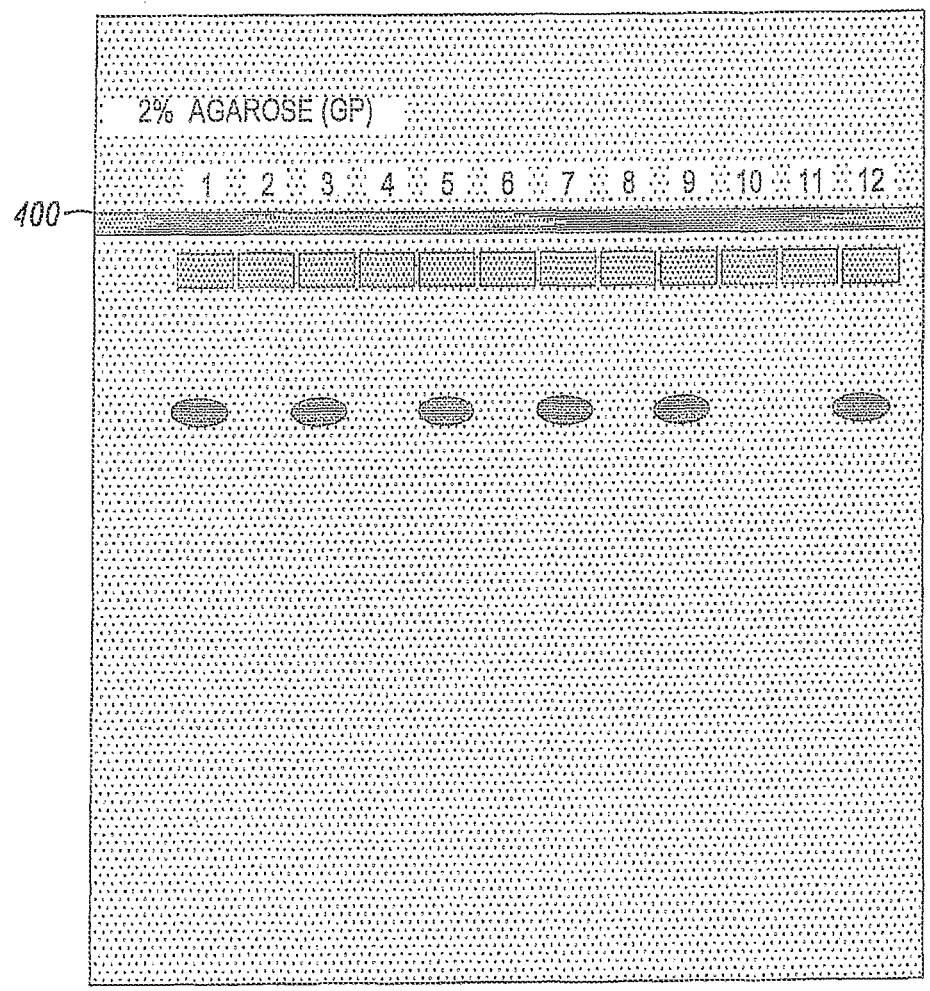
FIG. 10 is a redrawn image of a scanned gel in which fluorophore-stained nucleic acid molecules were separated in a gel illuminated with a blue light source using a first filter positioned between the light source and the gel, and a second filter positioned between the gel and the imaging system.
Figure 11:
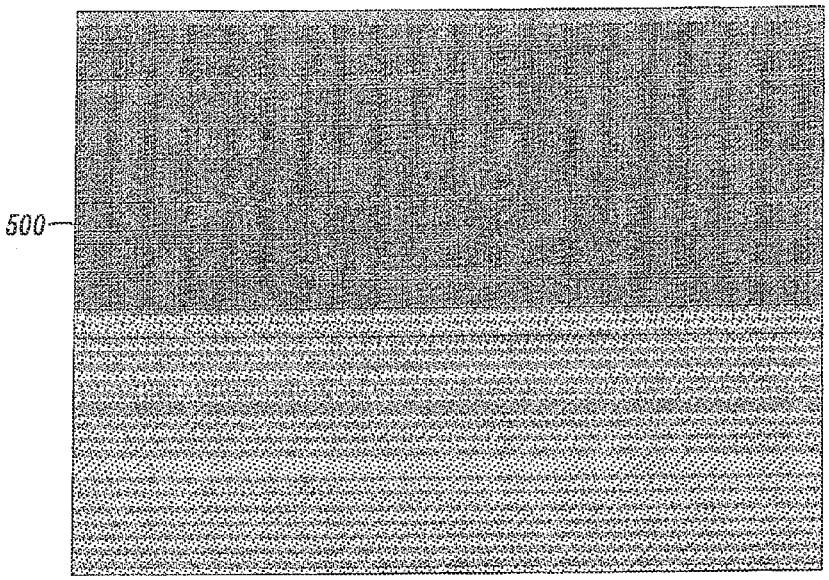
FIG. 11 is a redrawn image of fluorescent markings using a first filter positioned between the light source and the fluorophore, and a second filter positioned between the fluorophore and the imaging system.

Referring to FIG. 9, another embodiment of a device according to the invention is shown wherein, a flatbed scanner 300 is shown that is capable of imaging fluorescent gels. Modification of existing commercial flatbed scanning technology may be done to facilitate fluorescent imaging by the selective addition of excitation/emission filters and an appropriate LED light source. In one embodiment, a commercial flatbed scanner, such as CanoScan 8400F manufactured by Canon may be modified by replacing its current white light with a string of blue LEDs 302 with an appropriate blue excitation filter 304 on top of it to limit the excitation wavelength to below 500 nm. An emission filter 306 may be interposed between detector 308 and a sample 310 as shown in FIG. 9. Referring to FIG. 10, a reproduction of an image 400 taken from a scanner constructed according to one embodiment of the invention is shown. Reconstructed image 400 depicts a scanned image of a gel in which SYBR® Safe dye stained DNA bands were detected in an E-GEL® electrophoresis gel that included SYBR® Safe nucleic acid stain. The scanner was a commercially available white light source gel scanner used for gels stained with silver stain or COOMASSIE™ stain. The while lights were removed and replaced with a string of blue light emitting LEDs. A blue excitation filter was place over the light source, and an amber emission filter was placed over the cassette. Referring to FIG. 11, another image 500 depicts the detection of words written with a yellow highlighter (which is somewhat similar in fluorescent properties to SYBR® dyes) scanned with the same modified scanner.

Figure 12:
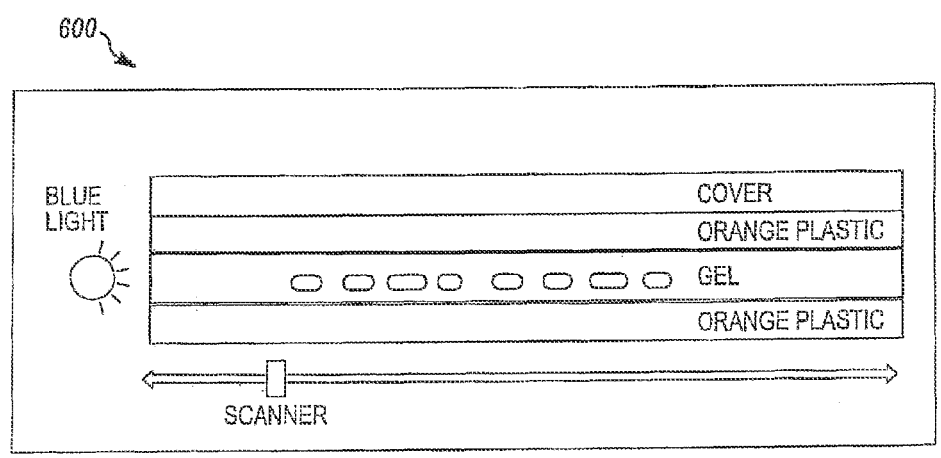
FIG. 12 is a schematic illustration of another system for electrophoresis imaging, constructed and operative in accordance with another embodiment of the present invention.

Referring to FIG. 12, another embodiment of an imaging system 600 according to the present invention is shown. In one variation, system 600 could be used wherein the emission filter is built directly into the precast gel cassette, as described above, except both the top and bottom plates or walls of the cassette could be an emission filter. Referring to FIG. 12, the gel may be exposed to excitation light form the side or lateral direction. One advantage of this configuration is that when a precast gel cassette with such a configuration is used with a scanner device it would permit the gel to be visualized from the top while an electronic image may be captured from below.

In another embodiment of a scanner or imaging device according to the present invention a built in power supply may be provided for running a gel electrophoresis experiment. This would allow the user to either monitor the run while it is in progress and stop and image when they deem appropriate, or it could even allow continuous monitoring of the electrophoretic run and image capture at the appropriate time (i.e. before the first band runs off of the end of the gel). A scanner/imaging device as described herein could also be programmed to automatically stop the electrophoresis run when, for example, a dye front from a loading dye or a stained band reached a certain distance, as monitored by the scanner.

In this regard, one skilled in the art will appreciate that it would also be possible to gather more data from gels utilizing such a configuration than conventional systems. The scanner could take multiple images as small molecular weight bands are run off the end of the gel while higher molecular weight bands are continued to be separated for maximal resolution—allowing a short 3 inch gel to provide the resolution of a 12 inch gel.

One skilled in the art will also appreciate that a significant advantage of modifying current flatbed scanner technology to fluorescent gel scanning capability is realizing the economies of scale to produce a low cost gel scanner. Significant cost benefits may be realized with the utilization of mass production flatbed scanners that are available to the public at, for example, office supply stores. With the foregoing modifications a typical scanner may be able to be modified to detect fluorescent samples.

Figure 13A:
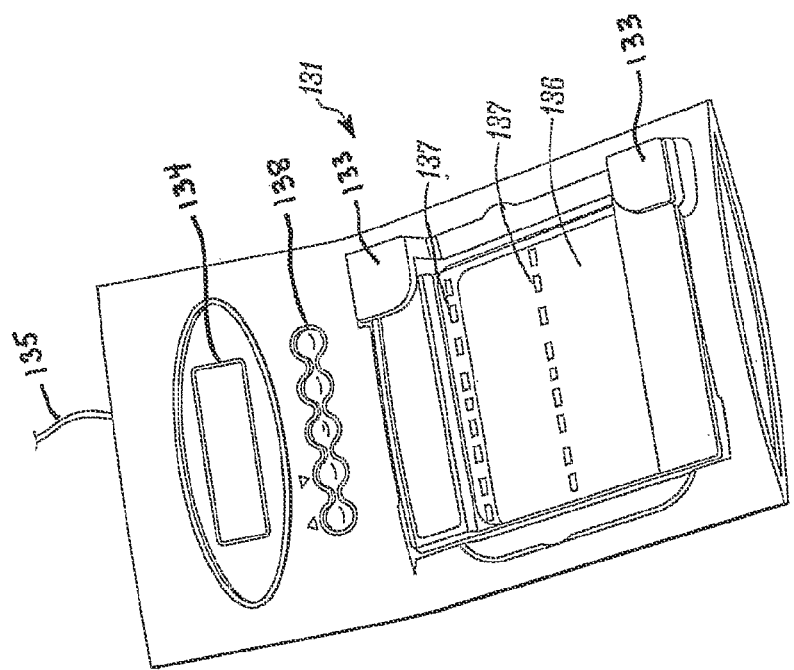
FIG. 13 is a depiction of a cassette electrophoresis base A) without a gel cassette, and B) with a gel cassette having two rows of wells and apertures.
Figure 13B:
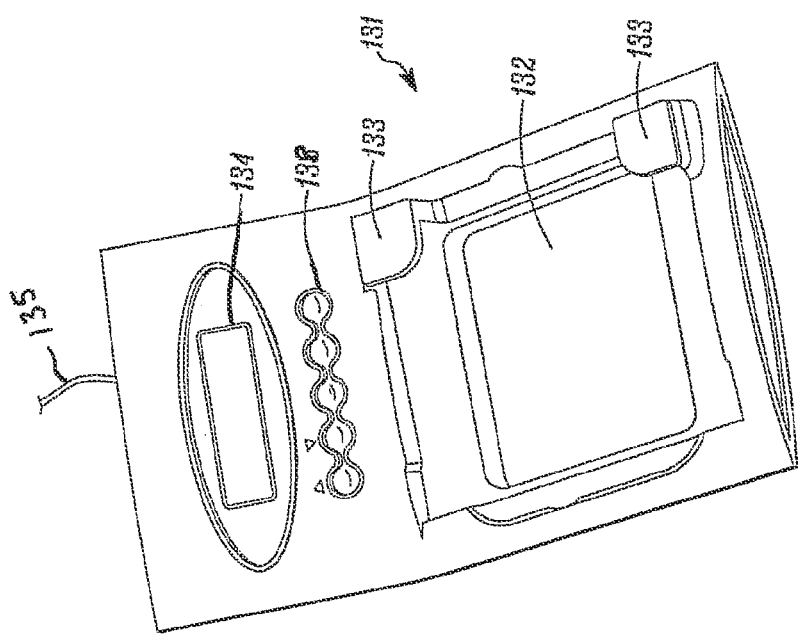

In another embodiment, FIG. 13A depicts one embodiments of a cassette electrophoresis base 131 showing the cassette positioning area 132 having corner pieces (133) into which the cassette can slide. The base has an LED display panel 134 and control switches 138 and is shown with an attached power cord 135. The base has an open space in the area a cassette would be positioned over during use of the base. In FIG. 13B, a cassette 136 having two rows of apertures 137 is shown positioned in the base.

Figure 14:
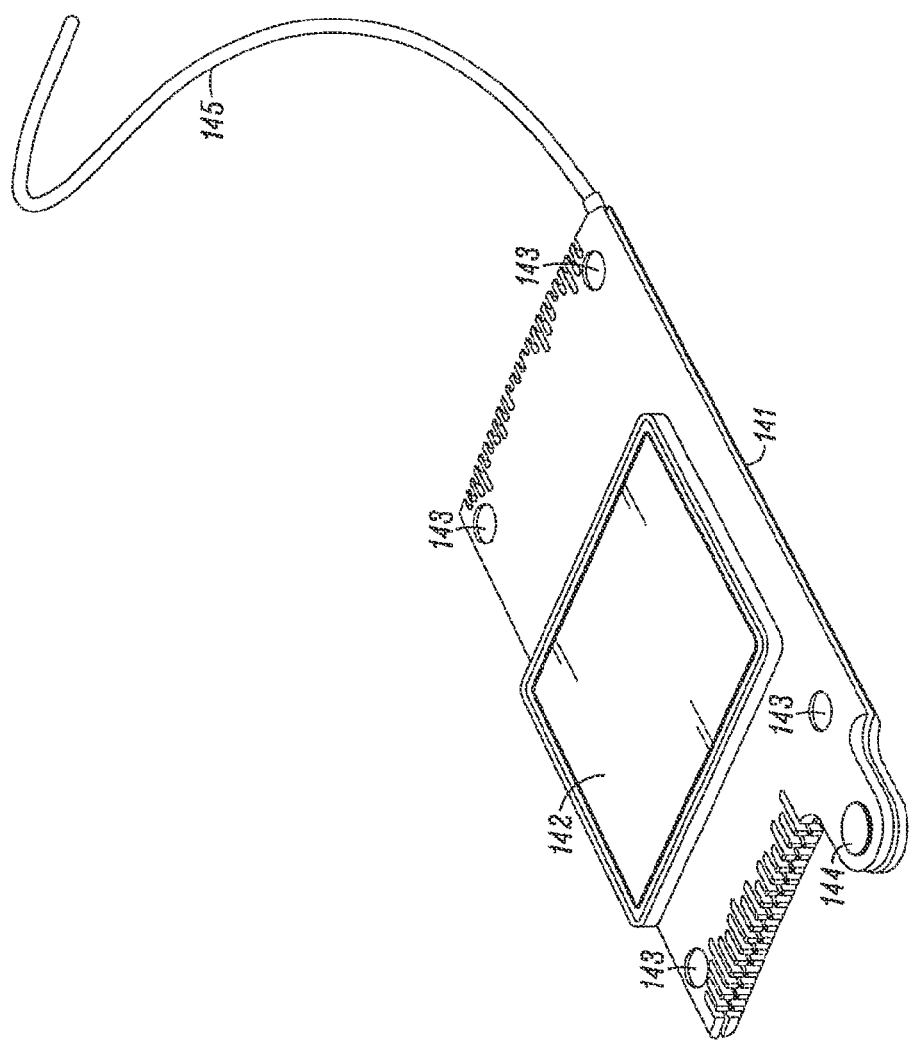
FIG. 14 is a drawing of A) a cassette electrophoresis base, B) a light source that can engage the electrophoresis base shown in A) and C) an electrophoresis system that includes the cassette electrophoresis base engaging the light source.

FIG. 14 depicts a light source base 141 that can be positioned under a base in certain aspects of the invention. The base has an LED array covered by one or more filters 142, depressions 143 for positioning a cassette electrophoresis base, an on/off switch 144, and a power cord 145.

Figure 15:
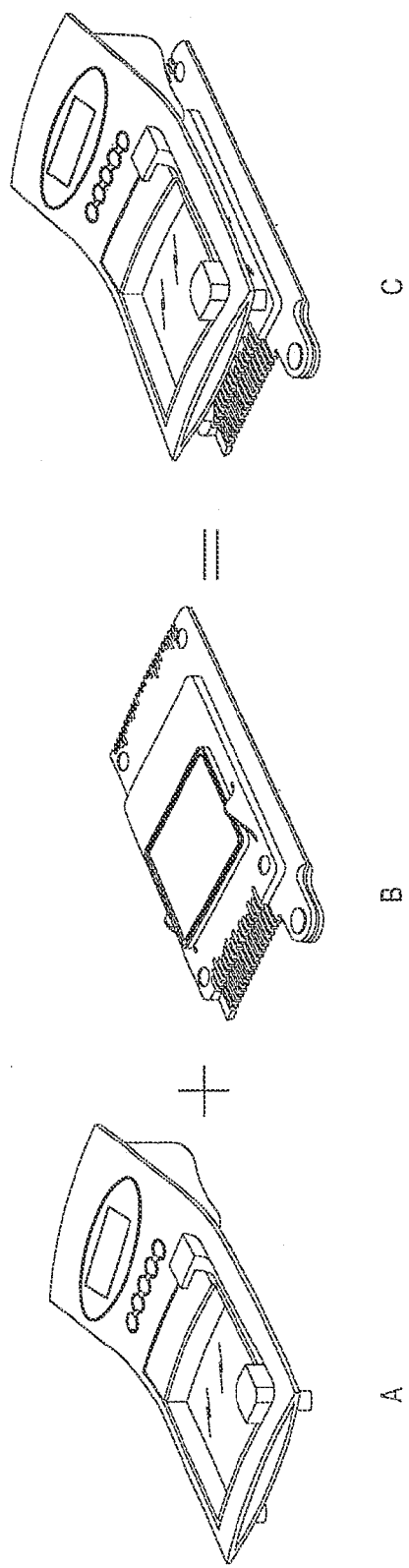
FIG. 15 is a depiction of a light source that can be used in combination with an electrophoresis cassette base of the invention.

FIG. 15A depicts a cassette electrophoresis base that includes a gel cassette. FIG. 15B depicts a light source base designed to reversibly engage the cassette electrophoresis base. FIG. 15 C depicts the cassette electrophoresis base positioned on the light source base.

Figure 16A:
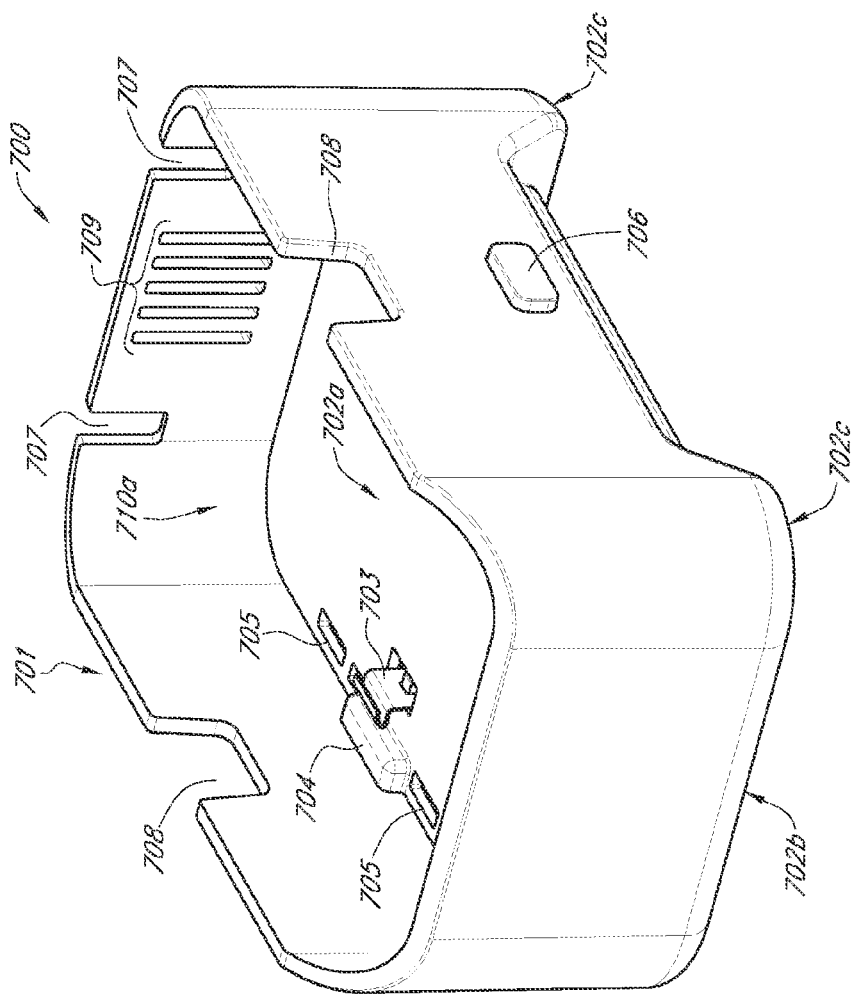
FIG. 16A depicts a schematic isometric inside view an charging device that is operable to charge an electrophoresis base, according to one embodiment of the disclosure.

In some embodiments, the present disclosure describes a charging device that is operable to charge an electrophoresis device including electrophoresis bases and electrophoresis systems to enable performing electrophoresis in the absence of an electrical connection. FIG. 16A depicts a schematic isometric view of a charging device 700 of the disclosure that is operable to charge an electrophoresis device/system. FIG. 16A depicts an example configuration of a charging device and has a cradle like configuration, disposing a cavity 710a, into which an electrophoresis device/system may be inserted. Charging device 700 comprises a battery which allows charging even in the absence of electrical power or electrical connectivity. In some embodiments, a rechargeable battery (including a battery pack) may be used in charging device 700. in some non-limiting embodiments, a charging device having a rechargeable battery may allow about 1.5 hours of operation for electrophoresis and gel illumination (which may cover about 5 gel runs).

The disclosure, however, is not limited to the exact device depicted in FIG. 16A and a charging device 700 of the disclosure may have several different configurations and shapes which may vary based on the shape and configuration of an electrophoresis device/system that is to be charged. In some embodiments, a charging device of the disclosure functions like a docking device wherein an electrophoresis device/system may be docked and charged while docking. In some embodiments, a charging device of the disclosure functions like a docking device wherein an electrophoresis device/system may be docked and electrophoresis may be carried out while docked.

Figure 16B:
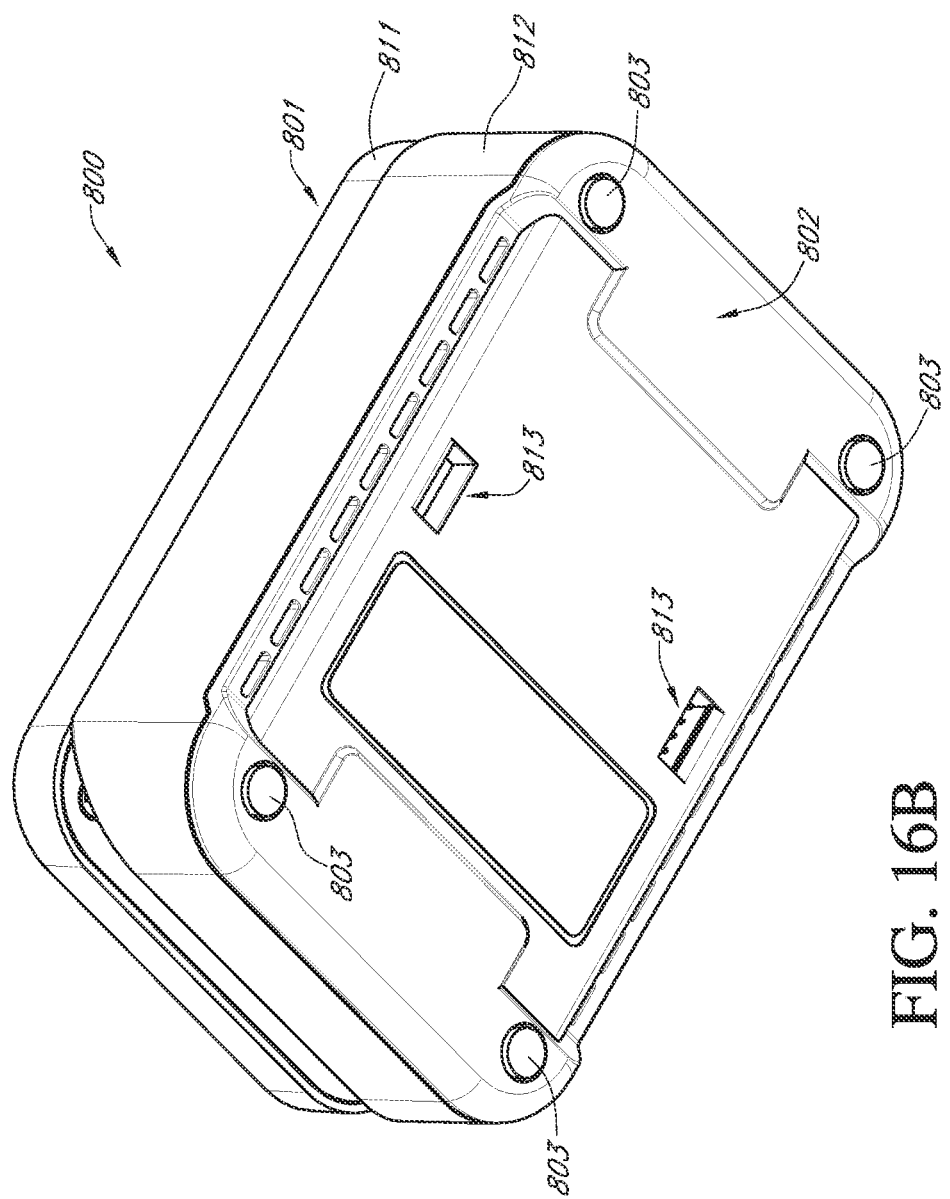
FIG. 16B depicts a schematic isometric view of the anterior side of an electrophoresis base that can fit into and be charged by the charging device of FIG. 16A, according to one embodiment of the disclosure.
Figure 18A:
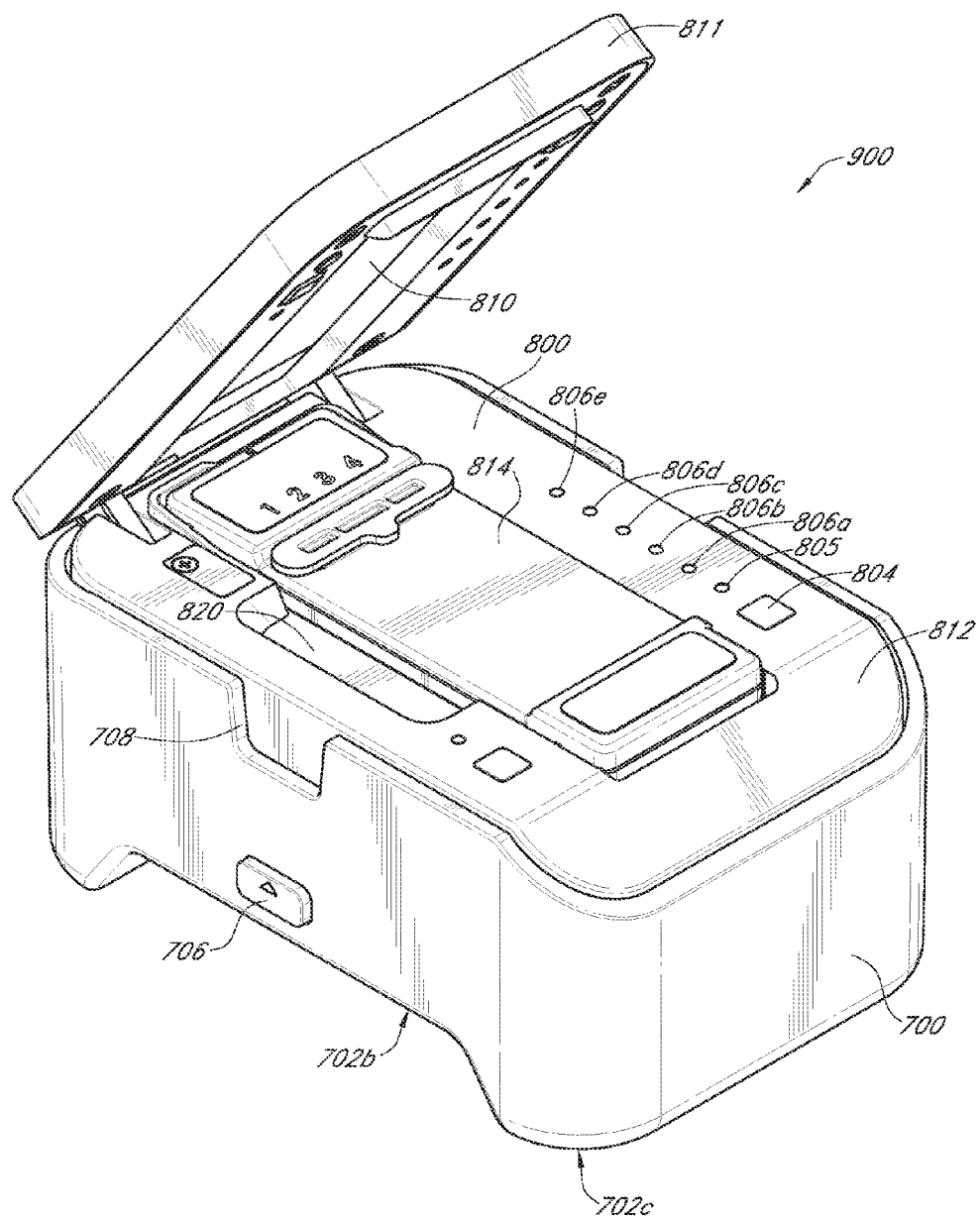
FIG. 18A depicts a schematic isometric view of an electrophoresis base docked in a charging device, according to one embodiment of the disclosure.
Figure 18B:
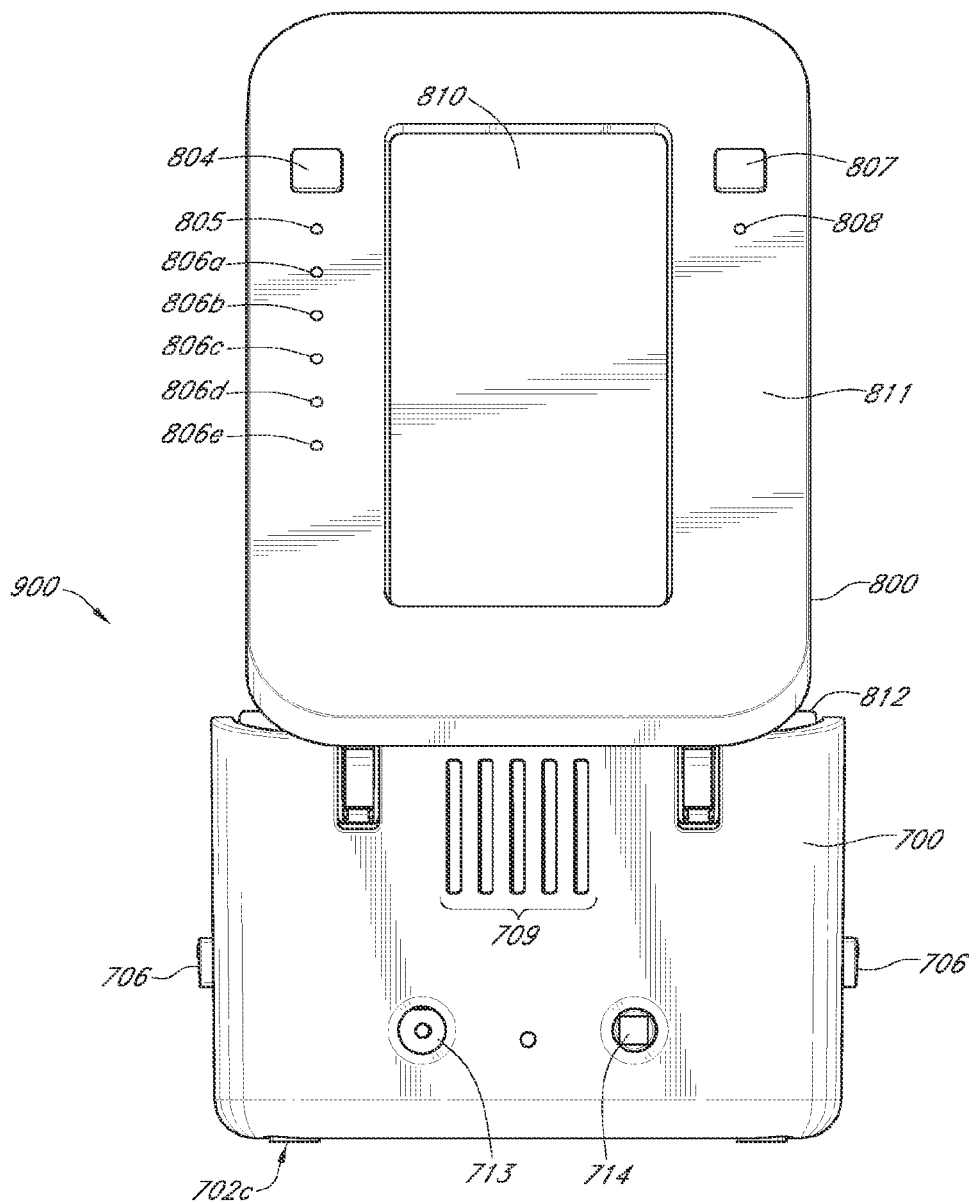
FIG. 18B depicts another schematic isometric view of an electrophoresis base docked in a charging base, according to one embodiment of the disclosure.

Some embodiments of charging devices of the disclosure are described using charging device 700 shown in FIG. 16A as an example and a corresponding or electrophoresis base/system 800 as shown in FIG. 16B (also see FIGS. 18A and 18B). In the foregoing description, electrophoresis system 800, may also be referred to as an electrophoresis base or an electrophoresis device. Several example electrophoresis bases and devices are described in this application and may comprise one or more components or devices such as but not limited to an electrophoresis device for running a gel, an automated electrophoresis device, an automated electrophoresis device that is easy-to-use and/or may be programmable, and/or has precast agarose gels and/or has pre-stained gels, and/or has a light transilluminator (e.g. blue light, UV light, visible light-based transilluminator) and/or has an imager, and/or a real time imager and/or a power supply. One or more of these components may be comprised in electrophoresis device/system 800.

FIG. 16A depicts charging device 700 having a receptacle/cradle/dock type configuration, shown as cavity 710a, that is operable to removably receive/insert an electrophoresis base 800. Charging device 700, has a top surface 701 and an interior lower surface 702a disposing a cavity 710a (also described as a receptacle/cradle/dock) therebetween.

Charging device 700 also has a battery chamber 710b (not expressly depicted in FIG. 16A, however, see FIGS. 21-24) that is disposed between interior lower surface 702a and exterior lower surface 702b. Charging device 700 may optionally have legs or supports 702c on which device 700 may rest on a surface.

Disposed on inner side of lower surface 702a are one or more connectors 703 that are operable to fit into corresponding complementary portions of an electrophoresis system 800 (such as part 813 in FIG. 16B and FIGS. 22-24) that may be placed into cavity 710b. In one embodiment, two connectors 703 may be present, one located on the left side of inner surface of lower side 702a and one on the right side of inner surface of lower side 702a (see also FIGS. 21-23). In some embodiments, additional connectors or complementary fitting receptacles may be present in charging device 700, such as 704 and 705. In some embodiments, connector 703 may provide mechanical connectivity between charging device 700 and electrophoresis system 800. In some embodiments, connector 703 may provide electrical connectivity between charging device 700 and electrophoresis system 800. In some embodiments, connector 703 may provide both mechanical connectivity and electrical connectivity between charging device 700 and electrophoresis system 800.

In some embodiments, charging device 700 may also have a plurality of grooves such as 707 and 708 that may be operable to help with receiving and docking the electrophoresis system 800. In some embodiments grooves 708 may allow a user to hold device 800 while placing said device into charging device 700. Charging device 700 may also have a plurality of openings or vents 709 that may be operable to cool electrophoresis system 800 during a run by providing a means for air circulation.

In some embodiments, charging device 700 may have one or more buttons on one or more external surfaces, shown for example as button 706, that may be configured to be pushed to release a docked electrophoresis device/system 800 from charging device 700 for removal after an electrophoretic run or when desired by an operator. Button 706 may also be configured to be pushed to attach and dock electrophoresis device/system 800 into charging device 700 for placement and docking to carry out an electrophoretic run or when desired by an operator. Thus, in some embodiments, button 706 may be a 2-way switch functioning to connect and release device 800 into and from device 700.

Button 706 may be operably connected to connector 703. In some embodiments, connector 703 fits to reciprocal connector receptacles (such as but not limited to 813, see in FIGS. 16B and 22-24) in electrophoresis system 800 and holds the electrophoresis system 800 in place. One or more connectors 703 may be present on the internal surfaces of 700 and may act as a mechanical connector between 700 and 800 and/or an electrical connector and/or both.

In some embodiments, connector 703 may be a clamp. In some embodiments, connector 703 may be a spring clamp. In some embodiments, two spring clamps 703 may be present on the left and right internal surfaces 702a and may act both as mechanical and electrical connectors. For example, electrophoresis system/base 800 can be placed or slipped into the cradle shaped cavity 710a of charging device 700 and clamps 703 can be locked upon pressing buttons 706 on one or both sides of charging device 700 to form a connection between the two devices. Electrophoresis system/base 800 may be disconnected, removed or dismounted by pressing the same button(s) 706 and pulling electrophoresis base 800 out of charging device 700.

Charging device 700 may also have LED Status Indicators located on external surfaces of device 700 (not expressly depicted) to visually display and indicate if the rechargeable battery of charging device 700 is fully charged or not. In one such embodiment, a green light indicates there is enough charge to complete at least one full gel run while a red light indicates there is not enough charge to perform a run. Additional components such as power outlets, USB outlets and others may be present to allow recharging of the rechargeable battery and for data transfer, connection to a camera, computer and/or other devices respectively.

FIG. 16B depicts a schematic isometric view of the anterior side of an electrophoresis base/system 800 that can removably fit into and be charged by charging device 700 (to perform electrophoresis and imaging) as shown in FIG. 16A, according to one embodiment of the disclosure. Electrophoresis system 800 is shown having a closed cover 811 disposed on top surface 801 and a cassette electrophoresis base 812. A plurality of rivets 803 (four rivets 803 are shown in FIG. 16B) on lower surface 802 may be used to place the device on a surface and in some embodiments to place on charging device 700. In some embodiments, charging device 700 may have corresponding complementary receptacles on its interior surface 702a to fit rivets 803 to maintain a snug connection. In some embodiments, at least one connector 813 may be present on the anterior surface of electrophoresis system 800 which may be operable to fit into connector 703 of charging device 700. In some embodiments, at least two connectors 813 may be present on the anterior surface of electrophoresis system 800 which may be operable to fit into connector 703 of charging device 700.

FIG. 17 depicts a schematic isometric view of a charging device 700 that is operable to charge an electrophoresis base/system 800 and depicts how electrophoresis base 800 would be aligned to be placed over charging device 700 to enable it to fit into cavity 710a of charging device 700. FIG. 17 depicts electrophoresis device 800 from the top. Electrophoresis base 800 is shown as an automated electrophoresis system having a transilluminator. Top view of electrophoresis system 800, as shown in FIG. 17, has a closed cover 811 disposed on top surface 801. Top surface 801, may have integrated into cover 811 one or more of these components: an amber filter unit 810; a Start button 804 operable to switch on electrophoresis system 800 and also operable to start programs and to toggle between time settings; a LED Status Indicator Light 805 to show the status of the electrophoresis system 800; a plurality of LED Time Indicator Lights 806 (shown in FIG. 17 as Five LED Time Indicator Lights 806a, 806b, 806c, 806d and 806e) operable to indicate the duration of a run (which may typically be a 5-20 minute run in 5 minute increments, each represented by one LED Time Indicator Light, for example 806a may represent a 5 minute run, 806b may represent a 10 minute run and 806c may represent a 15 minute run, however other settings of time may be created in device 800 and in some embodiments the last LED Time Indicator Light (such as 806e) may represent a longer run time for example a 30 minute run or a 45 minute run); a Light button 807 to turn a transilluminator on and off (such as a blue light transilluminator); and a LED Transilluminator Indicator 808 located just above Light button 807, to indicate the status of the blue light transilluminator. In some embodiments, a UV light transilluminator may be used in place of a blue light transilluminator.

FIGS. 18A and 18B, depict a portable electrophoresis system 900 of the disclosure comprising electrophoresis device 800 placed into docking/charging device 700 wherein lid/cover 811 is open. As shown in FIG. 18A, opening the cover of electrophoresis base 800 reveals a light transilluminator 820 (such as a blue light illuminator, or a UV illuminator) (that lies under gel cassette 814) for monitoring a gel run in real time (or after a run), and two electrode connections (not expressly shown) that make contact with gel cassette 814 (which may comprise an agarose gel, such as a precast agarose gel).

In some embodiments, electrophoresis system 800 of FIG. 18A may comprise one or more additional features, which are not expressly shown in the drawing, such as but not limited to: an array of 12 LED sources behind a blue filter that emit high intensity blue light; an internal battery allows the blue light transilluminator to be used to view gels for some time even when electrophoresis base 800 is not plugged in (e.g., 5 minutes or more, the internal battery automatically recharges during a run, or when device 800 is plugged in); a switch that automatically turns the transilluminator light off after 2 minutes; and a power inlet to accommodate a power supply cord of electrophoresis base 800; and/or an optional Car Adaptor. In some embodiments, electrophoresis system 800 may have a real-time integrated blue light transilluminator combined with an amber filter.

In some embodiments, in electrophoresis system 800, light from an array of 12 LED sources inside a transilluminator passes through a blue filter producing a single-intensity signal at approximately 480 nm, effective for the excitation of a blue light excitable fluorescent nucleic acid stain that may be used to stain agarose gels. In some embodiments, the blue light transilluminator utilizes an intense blue light for viewing gels, rather than UV light. The amber filter unit 810 in cover

811 provides a protective function and may be lowered by a user to protect their eyes while viewing gels.

Figure 20:
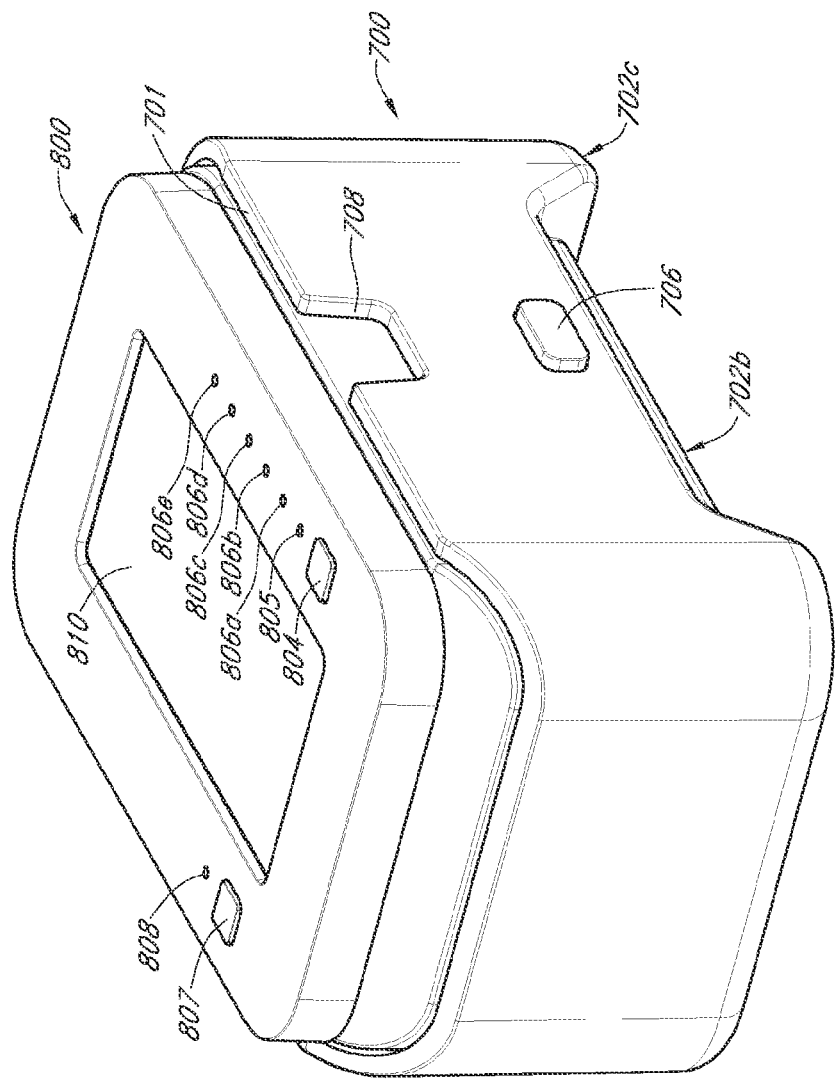
FIG. 20 depicts a schematic isometric view of a charging device connected to an electrophoresis base, according to one embodiment of the disclosure.

However, portable electrophoresis systems as shown in FIGS. 18A, 18B and 20 of the disclosure are not limited to using blue light transilluminators and may be instead used with a UV light transilluminator as well.

FIG. 18B depicts the back of portable electrophoresis system 900 as shown in FIG. 18A (and also FIG. 20) and shows the lid 811 of electrophoresis base 800 having the above described parts and features, and also shows the back of charging device/docking device 700 showing an outlet for power cable 713, an outlet for other connections 714 and a plurality of openings or vents 709, which are paralleled inside with corresponding vents and/or openings 818 (not expressly seen in picture) that are be operable to cool electrophoresis system 800 during a run by providing a means for air circulation. Openings or vents 818 when placed in charging device 700 lie adjacent to vents 709 in charging device 700. Other parts of docking device labeled include button 706 and legs 702c which are described above.

Figure 19:
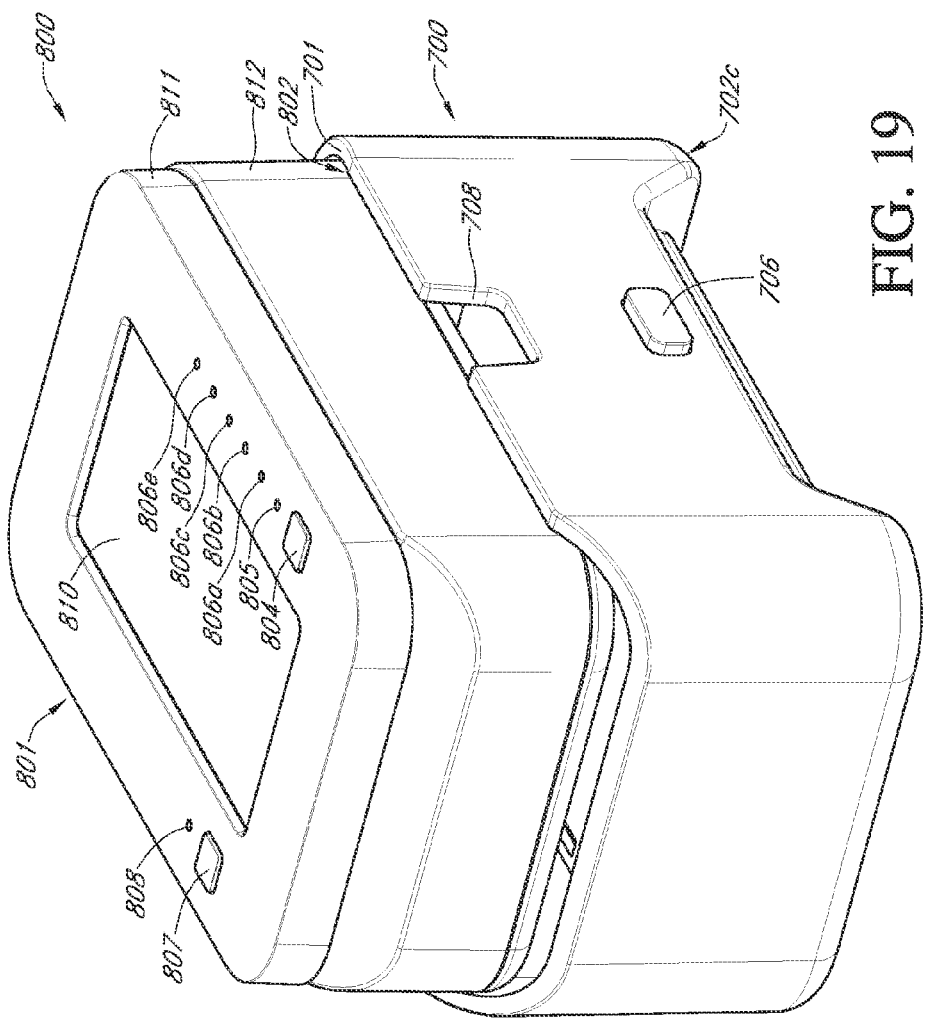
FIG. 19 depicts another schematic isometric view of a charging device that is operable to charge an electrophoresis base and an electrophoresis base as the electrophoresis base is being clamped into the charging device, according to one embodiment of the disclosure.

FIG. 19 depicts a schematic isometric view of charging device 700 that is operable to provide charge to an electrophoresis base 800 as the electrophoresis base 800 is being inserted into the charging device 700 according to one embodiment of the disclosure.

FIG. 20 depicts a schematic isometric view of a portable electrophoresis system 900 of the disclosure comprising charging device 700 operable to provide charge to an electrophoresis base 800 and shows electrophoresis base 800, with lid 811 closed, clamped into charging device 700 according to one embodiment of the disclosure. Charging device 700 is operable to provide charge to conduct several gel runs of electrophoresis device 800 in this configuration.

Figure 21:
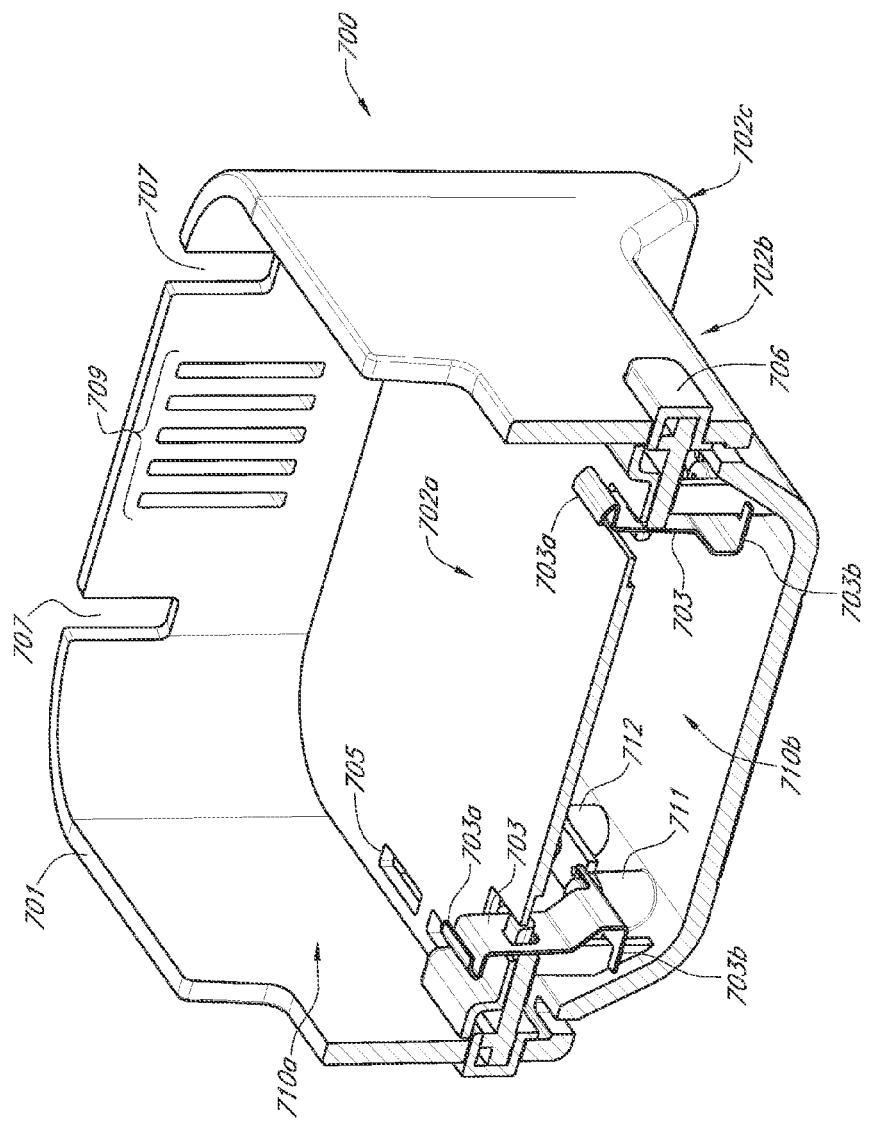
FIG. 21 depicts a schematic cross-sectional view a charging device that is operable to charge an electrophoresis base, showing the connection mechanisms operable to connect and facilitate charging, according to one embodiment of the disclosure.

FIG. 21 depicts a schematic cross-sectional view of charging device 700 showing connectors operable to connect/clamp to and facilitate charging of electrophoresis base 800, according to one embodiment of the disclosure. Cross sectional view of charging device 700 reveals a first chamber/receptacle/cavity 710a in between top surface 701 and inner lower surface 702a for placing an electrophoresis base 800 (not shown placed) and a second cavity which functions as battery chamber 710b. A connector 703 spans cavities 710a and 710b and passes through lower surface 702a. Top part 703a of connector 703 is operable to fit into a corresponding connector 813 on electrophoresis system 800 (not shown) and bottom portion 703b of connector 703 is shown to be in contact with 711 and 712 which may function as electrical and/or mechanical connectors.

FIG. 21 depicts charging device 700 having two connectors 703 one on the left side of cavity 710a and another on the right side of cavity 710a. Switch 706 that is operable to engage and disengage connector 703 with its corresponding receptacle in electrophoresis device 800 is also shown and its relation to connector is depicted. Other parts of FIG. 21 are described in sections above.

Figure 22:
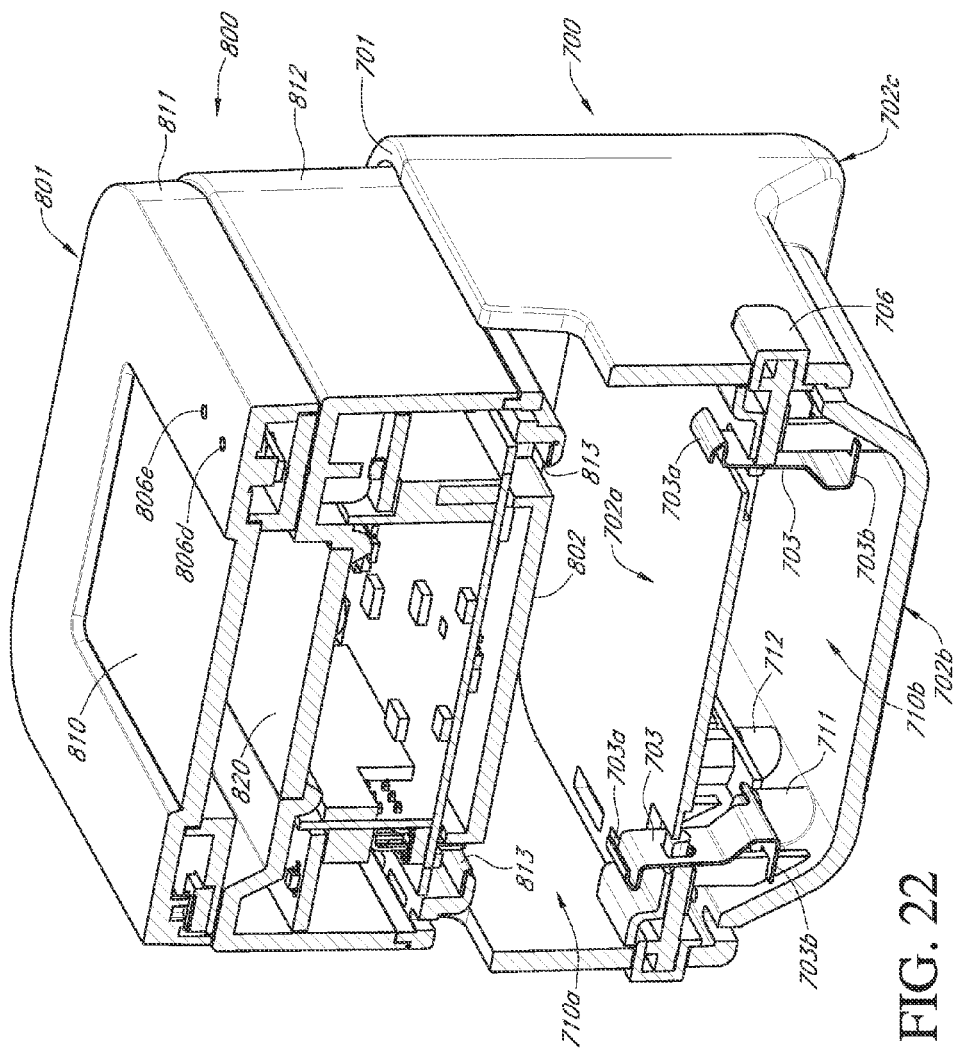
FIG. 22 depicts a schematic cross-sectional view of a charging device and cross-sectional view of an electrophoresis base showing mechanisms operable to connect to and facilitate charging of the two devices to each other, according to one embodiment of the disclosure.

FIG. 22 depicts a schematic cross-sectional view of charging device 700 and electrophoresis base 800, both devices aligned to be docked, showing the mechanisms that are operable to attach to and facilitate charging in both 800 and 700. Part numbers are similar to those described above.

Figure 23:
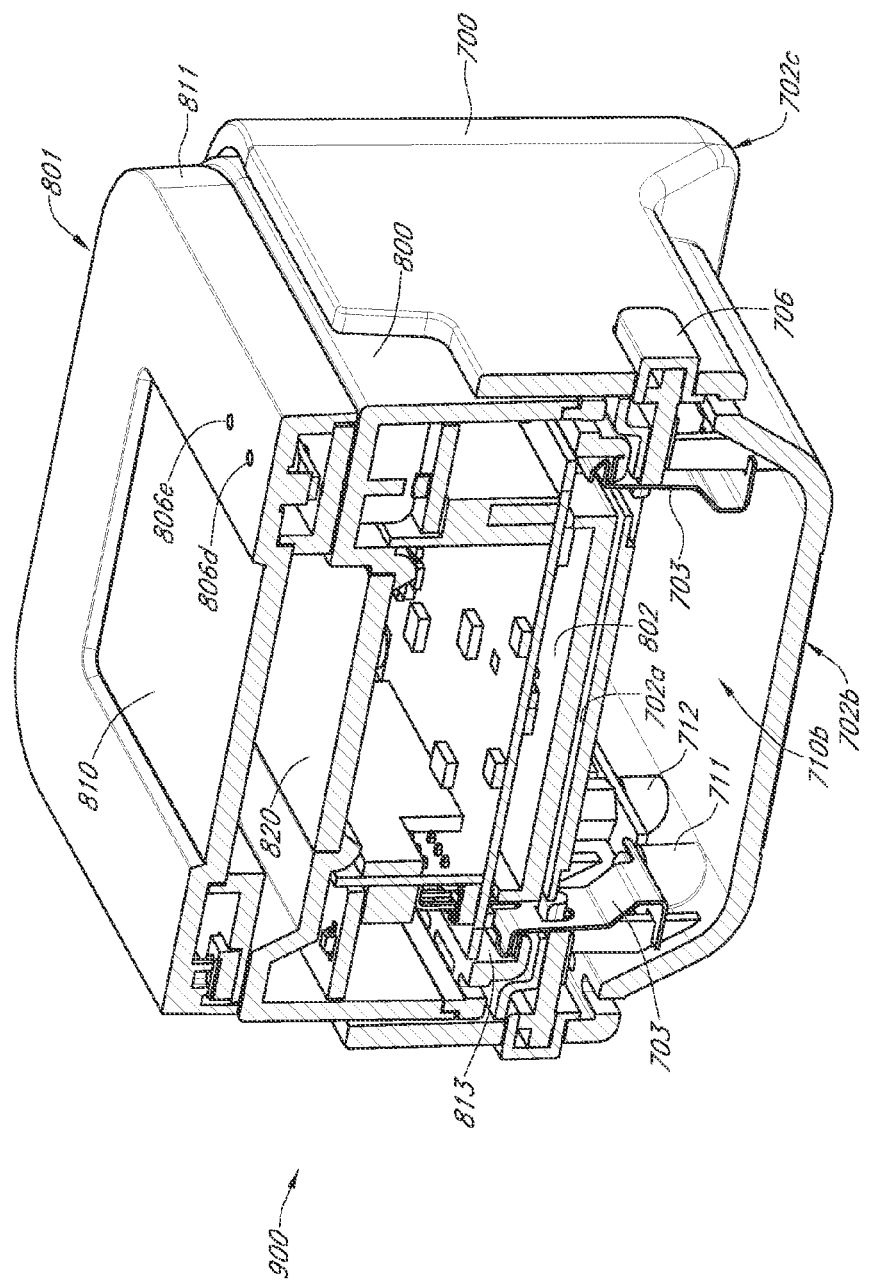
FIG. 23 depicts a schematic cross-sectional view of a connected electrophoresis base and a charging device showing the mechanisms for connection and facilitating charging, according to one embodiment of the disclosure.

FIG. 23 depicts a schematic cross-sectional view of electrophoresis base 800 now occupying first cavity 710a of charging device 700 to form portable electrophoresis system 900. FIG. 23 showing the mechanisms for attachment and connection and facilitating charging, according to one embodiment of the disclosure.

Figure 24:
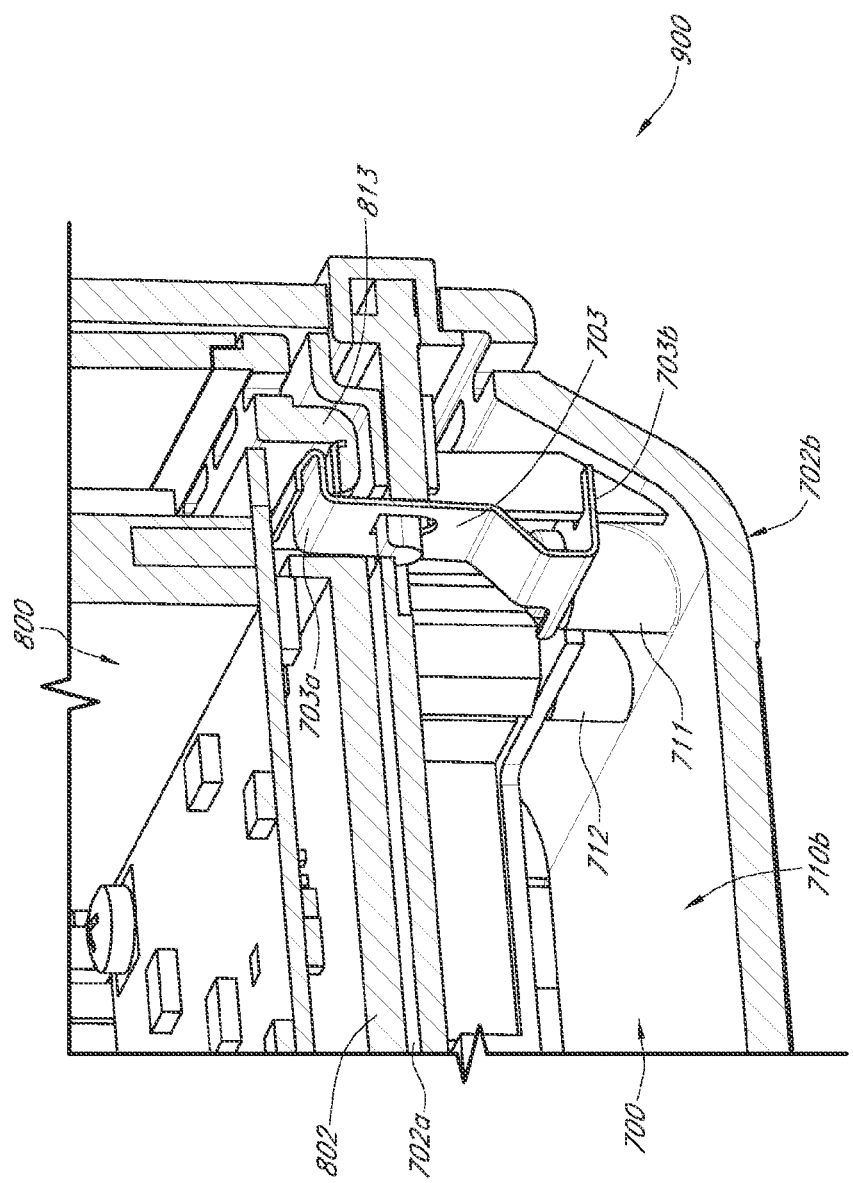
FIG. 24 depicts a schematic exploded cross-sectional view of clamped electrophoresis base and a charging device showing the mechanisms operable to form connections between the two devices and facilitate charging of the electrophoresis base, according to one embodiment of the disclosure.

FIG. 24 depicts a schematic exploded cross-sectional view of portable electrophoresis system 900 showing electrophoresis base now occupying receptacle 710a of charging device 700 and shows and exploded view of the mechanism that are operable to connect (mechanically and electrically) and facilitate charging of the electrophoresis base according to one embodiment of the disclosure.

In some embodiments, the disclosure provides a portable electrophoresis system 900, comprising a charging device (such as 700) and an electrophoresis device/base/system 800, wherein electrophoresis may be carried out at a site or a location where there is no electric power supply or during power outages. Electrophoresis systems of the disclosure, including a cassette electrophoresis base as described herein as well as electrophoresis systems that in addition to a cassette electrophoresis base further comprise an integral light source, in which the electrophoresis base also includes a gel imaging function may be used with the charging device of the disclosure to form a portable electrophoresis system. Portable electrophoresis systems of the disclosure are not limited to using blue light transilluminators and may be instead use a UV light transilluminator.

In some embodiments, a charging device and/or the portable electrophoresis system provide the convenience of performing electrophoresis at remote locations and may be useful in diagnostic, forensic and other applications at locations where a natural disaster or situation has caused power outages or at sites of field studies. Rechargable batteries may be pre-charged.

Figure 25:
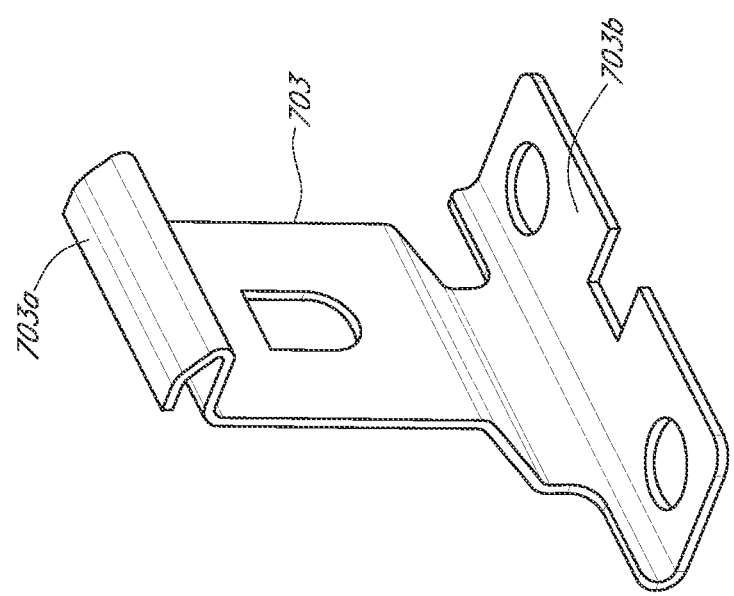
FIG. 25 depicts a connector that is operable to connect two devices together, according to one example embodiment of the disclosure.

FIG. 25 depicts connector 703 that is operable to connect two devices to each other. In one example a charging device as described herein or any docking type device may be connected using connector 703 with an electrophoresis device/base/system. Connector 703 comprises top portion 703a that has a bent configuration and may be operable to fit into a corresponding receptacle of a second device to which connection is sought. Lower portion 703b may be fashioned to have at least one connection to a first device. Connector 703 may be also described as an interlocking connector.

In some embodiments, connector 703 may provide mechanical connectivity between a first and a second device (for example, but not limited to charging device 700 and electrophoresis system 800). In some embodiments, connector 703 may provide electrical connectivity between a first and a second device. In some embodiments, connector 703 may provide both mechanical connectivity and electrical connectivity between a first and a second device.

In some embodiments, connector 703 may be a clamp. In some embodiments, connector 703 may be a spring clamp. In some embodiments, two spring clamps 703 may be present on a first device and corresponding receptacles may be present on a second device for connection. A spring clamp 703 may act both as a mechanical and an electrical connector. Connectors 703, including but not limited to spring clamps 703 may be further connected to a switch/button and may be locked to form a connection between two devices upon pressing one or more switch/button that is connected to connector 703. The two devices may be disconnected, removed or dismounted by pressing the same button(s)/switch and pulling a first device out of a second device.

Methods of using a portable electrophoresis device of the disclosure may comprise the following steps: placing an electrophoresis device 800 into the first cavity or cradle 710a of a charging device 700 that has a rechargeable battery; forming the electrical and mechanical connections between the electrophoresis device 800 and charging device 700; running electrophoresis in electrophoresis device 800; imaging an electrophoresed gel obtained from the electrophoresis of the previous step using an transilluminator and/or imaging system of the electrophoresis device 800; removing the electrophoresis device 800 from the cradle or cavity 710*a*.

Methods of using the portable electrophoresis system may comprise the step of verifying before beginning the method described above, that the rechargeable battery of the portable battery pack of a charging device 700 is fully charged and charging the battery if needed. In some embodiments this may be done by checking LED Status Indicators that may be present on device 700 (not expressly depicted). In such embodiments, a green light indicates there is enough charge to complete at least one full gel run while a red light indicates there is not enough charge to perform a run.

In some embodiments connecting and disconnecting charging device 700 with electrophoresis system 800 from cradle 710*a* may comprise pushing one or more buttons 706 located on one or more sides of charging device (pushing simultaneously if there are more than one buttons 706) to release system 800 from cradle 710*a*. A method may further comprise recharging the portable battery pack of charging device 700 by plugging the power cord attached thereto into a wall socket. A LED Status Indicator may blink green to indicate that the battery is recharging. When the battery is fully charged, the light may become a steady green. In some embodiments, a rechargeable battery of a portable electrophoresis system/charging device of the disclosure may take up to 4 hours to fully charge.

An portable electrophoresis device 900 as described in FIGS. 17, 19, 20, 23 and 24 having an automated gel electrophoresis device 800 may be used in methods of electrophoresis comprise at least a first step of preparing a gel for electrophoresis. This first step may comprise, if using a precast gel or a poured gel a user may remove the gel comb from the gel; insert the gel cassette into the electrophoresis device base; and ensure that the two electrodes on the right side of the gel cassette are in contact with the two electrode connections on the electrophoresis base. In an automated electrophoresis base/device/system 800 a LED Status Indicator Light 805 will illuminate with a steady red light to show that the gel cassette 814 is correctly inserted when the cover 811 is closed. The first step may also comprise steps of loading sample into the gel wells and in one non-limiting example embodiment may comprise: 1) Loading 10 μL of a prepared sample into sample wells; 2) Loading 10 μL of a marker DNA ladder into the desired marker wells (such as but not limited to E-Gel® 1 kb plus ladder for E-Gel® Go! 1% agarose gels; 1 Kb Plus DNA Ladder; or E-Gel® 50 bp DNA Ladder for E-Gel® Go! 2% agarose gels); 3) Loading 10 μL of deionized water into any remaining empty wells.

The method may comprise a second step of running a gel and may in a non-limiting example embodiment comprise selecting the run time for electrophoresis which may be done by pressing a Start button 804 and keeping the button depressed to select the time length of the gel run. Amber LED illuminates next to the LED Time Indicators to indicate the run time selected on the run, i.e., LED indicators 806 are light up, where lighting of LED indicator 806*a* indicates selection of a 5 minute run, lighting of LED indicator 806*b* indicates selection of a 10 minute run, lighting of LED indicator 806*c* indicates selection of a 15 minute run and so on. Since the LED indicators are visible on the lid/cover 811 of the electrophoresis base 800, one may stop depressing the button when the desired time is light up on the indicators 806. In general, setting for higher resolution runs (such as 30 minutes may be selected) to separate bands that are similar in size. Generally, automated devices of the disclosure allow setting a default run time setting such as 15 minutes, or show the last setting used on the electrophoresis base 800. Releasing button 804 when the desired run time is reached selects the desired run time.

To start the run the Start button 804 is pressed again to start the run. The red Status Indicator light 805 turns to a steady green light to show the start of the run. Typically, lid 811 must be closed for a gel run to start in device 800 of the disclosure. If the lid is opened during a run, the electrophoresis base 800 will automatically stop, the device will beep, and the Status Indicator Light 805 will blink red.

A method may comprise an optional third step of viewing the gel bands while the gel runs. For visualizing gel bands during a run in the method a used may press the Light button 807 on electrophoresis base 800. The LED Transilluminator Indicator 808 illuminates with a steady blue light when the transilluminator is on. Pressing the button a second time turns the transilluminator off.

As the gel run progresses, the amber LED lights 805 next to the run times indicator LEDs may turn off in 5 minute increments to indicate the amount of time remaining for the run. The run stops automatically after the programmed time has elapsed. The end of the run is signalled by the Status Indicator with a flashing red light and rapid beeping.

A gel run by the method described here may then be imaged or used for any other downstream application. To document results, any standard imaging device may be used. In some embodiments a blue light source and imaging setting for "SYBR" dyes may be used. It may also be possible to image the gel using transillumination from the E-Gel® Go! Base depending upon the optical configuration of the camera used. If blue light imaging is not possible, UV settings may be used.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

Example 1

The iBASE™ Power System

The E-GEL® iBASE™ Power System is an easy-to-use, programmable, automated device designed to simplify electrophoresis of single comb or double comb E-GEL® gels from Invitrogen (Carlsbad, Calif.). The E-GEL® iBASE™ Power System is a base for positioning and running a cassette and a power supply combined in one device.

The E-GEL® iBASE™ Power System has an LCD panel, which shows information about the program selected and running time. The display is located near the upper edge of the iBASE™ power supply. Just below the display, the E-GEL® iBASE™ Power System has four buttons: a Go button, to start programs; a Mode button, to toggle between programs, minutes, and seconds; an Up button (marked with an upward pointing triangle), to select between programs on the display and increase running time; a Down button (marked with a downward pointing triangle), to select between programs on the display and decrease running time; an LED light is located in the middle of the four buttons, which indicates the status of the iBASE™ power supply. At the back, the E-GEL® iBASE™ Power System contains a USB port and a power inlet. The supplied power cord has a matching connector that inserts into the power inlet, and connects the E-GEL® iBASE™ Power System to the electrical outlet. A separate, stand-alone power supply is not required to run the iBASE™ power supply.

The gel cassette is inserted into the two electrode connections at the lower half of the iBASE™ power supply.

The iBASE™ power supply is pre-programmed with 7 different programs for running the various types of E-GEL® gels. Toggle between program, minutes, and seconds by pressing the Mode button (M) until the program blinks. Select the appropriate program for the gel type using the Up/Down buttons to change the program. If you want to change the run time, press the Mode button until the minutes or seconds blink and change the values using the Up/Down buttons (up to the maximal run time indicated below). The iBASE™ program can be reset by pressing and holding the Go button for three seconds until the display reads "E-GEL iBASE".

The iBASE™ is pre-programmed with a program for quick runs to get a "yes/no" result. The program "SPEED E-GEL" utilizes high power and is suitable for 0.8%, 1.2% and 2% E-GEL® gels. This program is limited to 7 minutes, where the bands migrate less than half the length of the gel. A run exceeding 7 minutes, under these conditions results in a defective run.

Open the package and remove the gel cassette. Slide the cassette into the two electrode connections on the E-GEL® iBASE™ Power System. Press on the left side of the cassette to secure it into the iBASE™. The two electrodes on the right side of the gel cassette must be in contact with the two electrode connections on the base. The LED light will illuminate a steady red to show that the cassette is correctly inserted. Select the program PRE-RUN 2 min and press the Go button to pre-run the gel. The LED light changes to green light to indicate that the cassette is in the pre-run mode. After two minutes pre-run stops automatically as indicated by a red light and a beeping sound.

Select the appropriate program according to the table on the previous page. Take out the comb and load your samples according to the E-GEL® manual. Be sure to load molecular weight markers and add water to any empty wells (as directed by the E-GEL® manual).

To start electrophoresis press the Go button, a green light illuminates to show that the run is in progress. The LCD displays the count down time while the run is in progress. The run will stop automatically when the programmed time has elapsed. The iBASE™ power system signals the end of the run with a flashing red light and rapid beeping for 30 seconds followed by a single beep every minute. The LCD displays "Run Complete Press Go". Press and release the Go button to stop the beeping. The light turns to a steady red light and the LCD display shows the last selected time and program.

Remove the E-GEL® cassette from the iBASE™. You are now ready to proceed to imaging or any other application with the gel. The E-GEL® iBASE™ power system is pre-programmed with a program to run E-GEL® gels in a reverse direction. This is particularly useful for isolating fragments using E-GEL® CloneWell™ agarose gels. Toggle between program, minutes, and seconds by pressing the Mode button (M) until the program blinks. Select the "REVERSE E-GEL" Program using the Up/Down buttons to change the program. If you want to change the run time, press the Mode button until the minutes or seconds blink and change the values using the Up/Down buttons (the maximal run time for reverse running is 3 minutes). To start electrophoresis press the Go button, a green light will illuminate to show that the run is in progress. The LCD display will show the count down time while the run is in progress. The iBASE™ will signal the end of the run with a flashing red light and rapid beeping for 30 seconds followed by a single beep every minute, while the LCD display will read "Run Complete Press GO". Press and release the Go button to stop the beeping. The light turns to a steady red light and the LCD display shows the last selected time and program. Remove the E-GEL® cassette from the iBASE™ power system. You are now ready to proceed to imaging or any other application with the gel.

Example 2

The E-GEL® SAFE IMAGER™ Transilluminator

The E-GEL® SAFE IMAGER™ light source base can be powered and used independently of the E-GEL® iBASE™ power system by means of a power cord with AC/DC adapter that can be plugged into a wall outlet, or can be used with and powered by the E-GEL® iBASE™ Power System by connecting a short electrical cord ("tether") from a power cord inlet on the E-GEL® SAFE IMAGER™ light source base to a power cord inlet on the E-GEL® iBASE™ power system, which then connects via a power cord plus AC/DC adapter to a wall outlet.

The E-GEL® SAFE IMAGER™ transilluminator can be used for visualizing stained molecules or cells in gels (in cassettes placed on the light source base, or not in cassettes), plates, wells, on membranes, filters, or slides. Imaging of a gel, cassette, membrane, dish, etc, placed on the viewer can be by means of any feasible imaging system, including a conventional or digital camera. An amber filter can be placed over the sample material for viewing or imaging, or a user can wear amber goggles, or a camera or viewpiece can include an amber filter.

To install the E-GEL® SAFE IMAGER™ transilluminator on its own (without a cassette base), first ensure that the E-GEL® SAFE IMAGER™ real-time transilluminator is placed on a level bench and that there is enough air circulation around the unit to prevent overheating. Plug the connecting end of the power cord with the transformer into the back inlet of the E-GEL® SAFE IMAGER™ transilluminator and connect the power cord to the electrical socket. The short electrical cord in this case stays disconnected. A steady, red light will illuminate when the E-GEL® SAFE IMAGER™ transilluminator is connected to the electricity correctly and is ready to use.

The iBASE™ power system can also be positioned on the E-GEL® SAFE IMAGER™ light source base during electrophoresis (see FIGS. 13-15) to view the stained bands as the gel runs. The E-GEL® SAFE IMAGER™, light source base comprising 12 blue light emitting LEDs and a blue excitation filter, can be turned on to illuminate an E-GEL® cassette that includes a blue light absorbing dye, for example a SYBR® dye such as SYBR® Safe nucleic acid stain.

A user can view separating biomolecules using an amber emission filter that is provided as a separate piece that can be placed over the cassette region of the iBASE™ power system. In the alternative, an amber filter can be incorporated into the upper wall of a cassette used in the iBASE™ or a user can view the gel using amber viewing glasses. A user can also image the gel with a detection device, such as a camera (for example, a digital camera), that can be positioned over the cassette. The camera can be part of an imaging and documentation system that can produce an image that can be viewed on a screen, printed, stored, and/or electronically transmitted to a separate computer, such as a personal computer.

To install the E-GEL® SAFE IMAGER™ light source base with the E-GEL® iBASE™ power system, position the device such that the power inlet located on the rear of the unit is easily accessible, to be able to safely connect and disconnect the power cord to the E-GEL® iBASE™ power system. Attach the power cord to the power inlet of the light source base and then to the electrical outlet. Use only properly grounded AC outlets and power cords. The fan in the device begins, the LED (yellow) and LCD are activated. The fan and LED will turn off after 3 seconds if no gel is inserted. The LCD initially displays the software version which changes within a few seconds to display the default parameters (PRE-RUN 2 minutes) or the last used program and time setting.

Place the iBASE™ cassette runner directly onto the E-GEL® SAFE IMAGER™ real-time Transilluminator so that the legs of the iBASE™ power system fit directly into the grooves of the SAFE IMAGER™ transilluminator. Plug the E-GEL® SAFE IMAGER™ real-time Transilluminator short electrical cord into the iBASE™ runner's power inlet.

Plug the connecting end of the power cord with the transformer into the back inlet of the SAFE IMAGER™ light source base and connect the power cord to the electrical socket. A steady, red light will illuminate when the E-GEL® SAFE IMAGER™ transilluminator is connected to the electricity correctly and is ready to use. The fan in the iBASE™ power system begins, the LED (yellow) and LCD are activated. The fan and LED on the iBASE™ power system will turn off after 3 seconds if no gel is inserted. The LCD initially displays the software version which changes within a few seconds to display the default parameters (PRE-RUN 2 minutes) or the last used program and time setting.

To view the gel containing a blue-light activatable dye (for example, a gel containing nucleic acid such as DNA molecules stained with a SYBR® dye), place the Amber filter unit on top of the cassette region of the iBASE™ gel cassette runner, or use amber-filter containing viewing glasses (for example, when excising bands from DNA gels). The E-GEL® SAFE IMAGER™ amber filter unit or E-GEL® SAFE IMAGER™ viewing glasses help to visualize SYBR®-Safe stained DNA, and also prevent prolonged exposure of the eyes to the intense blue light of the iBASE™ transilluminator. The E-GEL® SAFE IMAGER™ transilluminator can be switched on using the ON/OFF button in one of these ways: 1) To turn on the light for 30 seconds press and release the ON/OFF button. The LED indicator light will be a flashing green throughout the run; 2) To turn on the light for 5 minutes press and hold the ON/OFF button for a few seconds. The LED indicator light will turn a steady green followed by a flashing green the last 30 seconds of the run. Any SYBR®-Safe stained DNA present should be immediately visible after light is on and amber filter unit or viewing glasses are in position. To turn off the light, press and release the ON/OFF button. The LED indicator light will turn red.

To document results any standard imaging device can be used. Due to the small footprint, the E-GEL® SAFE IMAGER™ real-time transilluminator may fit inside the cabinet of currently available gel documentation systems. The documentation can be performed with or without the iBASE™ power system unit on the SAFE IMAGER™ transilluminator. In many cases, satisfactory results are obtained by placing the amber filter unit on top of the gel and photographing/imaging as normal. The distance between the camera and the gel may have to be adjusted. In addition some CCD documentation systems may include a filter that will work in place of the amber filter unit (contact the manufacturer for filter specifications). To document gels with other stains compatible with the E-GEL® SAFE Imager™ real-time transilluminator please refer to the directions on imaging conditions and filters in the instruction manual of the relevant stain.

While the invention herein disclosed has been described by means of specific embodiments and applications thereof, numerous modifications and variations can be made thereto by those skilled in the art without departing from the scope of the invention.

All references cited herein, including patents, patent applications, and printed publications are incorporated herein in their entireties.

What is claimed is:

1. A charging device operable to charge an electrophoresis device comprising:
   a receptacle having at least one cavity configured to accommodate an electrophoresis device;
   at least one connector operable to provide electrical connectivity to the electrophoresis device, wherein the connector is a clamp;
   at least one switch operable to removable engage the connector to form a connection with the electrophoresis device; and
   a rechargeable battery in electrical connection with the connector, whereby the electrophoresis device may be charged to enable electrophoresis.

2. The charging device of claim 1, the connector further providing mechanical connectivity to the electrophoresis device.

3. The charring device of claim 1, the connector having at least a first end having a configuration complementary to a receptacle in the electrophoresis device, whereby the first of the connects fits into the receptacle of the electrophoresis device.

4. The charging device of claim 1, wherein the connector is a spring clamp.

5. The charging device of claim 1, having at least two connectors.

6. The charging device of claim 1, having at least two switches.

7. The charging device of claim 1, further comprising a power connection to recharge the rechargeable battery.

8. The charging device of claim 1, wherein the electrophoresis device comprises an automated electrophoresis device; a transilluminator; an imaging system or any combinations thereof.

9. The charging device of claim 1, wherein the electrophoresis device uses pre-cast gels.

10. A portable electrophoresis system comprising:
    a charging device operable to provide charge to an electrophoresis device to enable electrophoresis, the charging device comprising:
      a receptacle having at least one cavity configured to accommodate an electrophoresis device;
      at least one connector operable to provide electrical connectivity to the electrophoresis device;
      at least one switch operable to removable engage the connector to form a connection with the electrophoresis device;
      a rechargeable battery in electrical connection with the connector; and an electrophoresis device, wherein the electrophoresis device comprises a transilluminator.

11. The portable electrophoresis system of claim 10, the charging device further comprising a power connection to recharge the rechargeable battery.

12. The portable electrophoresis system of claim 10, wherein the electrophoresis device comprises an automated electrophoresis device.

13. The portable electrophoresis system of claim 10, wherein the electrophoresis device comprises an imaging system.

14. The portable electrophoresis system of claim 10, wherein the electrophoresis device uses pre-cast gels.

15. The portable electrophoresis system of claim 10, the connector having at least a first end having a configuration complementary to a receptacle in the electrophoresis device, whereby the first end of the connects fits into the receptacle of the electrophoresis device.

16. A method for performing electrophoresis comprising:
    placing an electrophoresis base into a portable docking device the portable docking device having a rechargable battery pack;
    loading a gel with a sample that is to be separated by electrophoresis;
    forming an electrical connection between electrodes of the electrophoresis base and the portable docking device;
    running electrophoresis to separate the components of the sample, wherein the electrophoresis is performed at a location where electrical connectivity is unavailable; and
    imaging the resolved components of the sample, wherein the imaging is real-time imaging.

17. A portable electrophoresis system comprising:
    a charging device operable to provide charge to an electrophoresis device to enable electrophoresis, the charging device comprising:
        a receptacle having at least one cavity configured to accommodate an electrophoresis device;
        at least one connector operable to provide electrical connectivity to the electrophoresis device;
        at least one switch operable to removable engage the connector to form a connection with the electrophoresis device;
        a rechargeable battery in electrical connection with the connector; and
    an electrophoresis device, wherein the electrophoresis device comprises an imaging system.

18. A charging device operable to charge an electrophoresis device comprising:
    a receptacle having at least one cavity configured to accommodate an electrophoresis device;
    at least one connector operable to provide electrical connectivity to the electrophoresis device, wherein the connector is a spring clamp;
    at least one switch operable to removable engage the connector to form a connection with the electrophoresis device; and
    a rechargeable battery in electrical connection with the connector, whereby the electrophoresis device may be charged to enable electrophoresis.

* * * * *